(12) United States Patent
Hoogboom et al.

(10) Patent No.: US 12,331,239 B2
(45) Date of Patent: Jun. 17, 2025

(54) COMPOSITION AND PROCESS FOR SELECTIVELY ETCHING A LAYER COMPRISING AN ALUMINIUM COMPOUND IN THE PRESENCE OF LAYERS OF LOW-K MATERIALS, COPPER AND/OR COBALT

(71) Applicant: BASF SE, Ludwigshafen am Rhein (DE)

(72) Inventors: Joannes Theodorus Valentinus Hoogboom, Ludwigshafen (DE); Jhih Jheng Ke, Taoyuan (TW); Che Wei Wang, Taoyuan (TW); Andreas Klipp, Ludwigshafen (DE); Yi Ping Cheng, Taoyuan (TW)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 18/519,571

(22) Filed: Nov. 27, 2023

(65) Prior Publication Data

US 2024/0093089 A1    Mar. 21, 2024

Related U.S. Application Data

(63) Continuation of application No. 16/765,371, filed as application No. PCT/EP2018/083683 on Dec. 5, 2018, now abandoned.

(30) Foreign Application Priority Data

Dec. 8, 2017  (EP) ..................................... 17206096
Jun. 28, 2018 (EP) ..................................... 18180361

(51) Int. Cl.
   C23F 1/20       (2006.01)
   C07D 265/30     (2006.01)
   C09K 13/00      (2006.01)
   C23F 1/44       (2006.01)
   H01L 21/311     (2006.01)

(52) U.S. Cl.
   CPC ............ *C09K 13/00* (2013.01); *C07D 265/30* (2013.01); *C23F 1/20* (2013.01); *C23F 1/44* (2013.01); *H01L 21/31111* (2013.01)

(58) Field of Classification Search
   None
   See application file for complete search history.

(56) References Cited

U.S. PATENT DOCUMENTS

| | | | |
|---|---|---|---|
| 5,200,114 A * | 4/1993 | Beck ........................ | C23G 1/22 510/237 |
| 6,696,222 B2 | 2/2004 | Hsue et al. | |
| 8,765,654 B2 | 7/2014 | Minsek et al. | |
| 9,063,431 B2 | 6/2015 | Barnes et al. | |
| 2004/0061092 A1 | 4/2004 | Brankovic et al. | |
| 2006/0014391 A1 * | 1/2006 | Lee ........................ | C11D 7/3281 438/695 |
| 2006/0172906 A1 | 8/2006 | Wu et al. | |
| 2008/0051308 A1 * | 2/2008 | Kane ........................ | C11D 7/5013 510/176 |
| 2008/0261847 A1 | 10/2008 | Visintin et al. | |
| 2009/0215658 A1 | 8/2009 | Minsek et al. | |
| 2010/0044624 A1 * | 2/2010 | Wilken ..................... | C09D 5/20 252/79.1 |
| 2010/0075478 A1 | 3/2010 | Chang | |
| 2011/0217833 A1 | 9/2011 | Lee et al. | |
| 2011/0275164 A1 | 11/2011 | Visintin et al. | |
| 2012/0052686 A1 | 3/2012 | Liu et al. | |
| 2013/0296214 A1 * | 11/2013 | Barnes .............. | H01L 21/02063 510/176 |
| 2015/0000697 A1 | 1/2015 | Minsek et al. | |
| 2015/0307818 A1 | 10/2015 | Barnes et al. | |
| 2016/0130500 A1 | 5/2016 | Chen et al. | |
| 2016/0153094 A1 * | 6/2016 | Tuteja ..................... | C23C 22/73 216/53 |
| 2016/0185595 A1 * | 6/2016 | Chen ........................ | G03F 7/405 252/79.3 |
| 2017/0107460 A1 | 4/2017 | Liu et al. | |
| 2018/0251711 A1 | 9/2018 | Liu et al. | |

FOREIGN PATENT DOCUMENTS

| | | |
|---|---|---|
| EP | 3089200 B1 | 5/2020 |
| JP | 2002241795 A | 8/2002 |
| JP | 2013533631 A | 8/2013 |
| TW | 201209156 A | 3/2012 |
| TW | 201510180 A | 3/2015 |
| TW | 201710556 A | 3/2017 |

(Continued)

OTHER PUBLICATIONS

Danish Ministry of the Environment "Benzotriazole and Tolyltriazole" via https://www2.mst.dk/Udgiv/publications/2013/12/978-87-93026-81-0.pdf, pp. 1-28 (2013).
Wikipedia "N-Methylmorpholine N-oxide" via https://en.wikipedia.org/wiki/N-Methylmorphonline_N-oxide (2023).
"4-Ethylphorpholine 4 oxide" via https://pubchem.ncbi.nlm.nih.gov/compunt/4-Ethylmorpholine-4-oxide, pp. 1-22.

(Continued)

*Primary Examiner* — Binh X Tran
(74) *Attorney, Agent, or Firm* — Armstrong Teasdale LLP

(57) ABSTRACT

A composition for selectively etching a layer including an aluminum compound in the presence of a layer of a low-k material and/or a layer including copper and/or cobalt, and a corresponding process, are described. Further described is a process for the manufacture of a semiconductor device, including the step of selectively etching at least one layer including an aluminum compound in the presence of a layer of a low-k material and/or a layer including copper and/or cobalt by contacting the at least one layer including an aluminum compound with the described composition.

19 Claims, No Drawings

(56) References Cited

FOREIGN PATENT DOCUMENTS

| | | |
|---|---|---|
| WO | 2003035797 A1 | 5/2003 |
| WO | 2004030038 A2 | 4/2004 |
| WO | 2009064336 A1 | 5/2009 |
| WO | 2012009639 A2 | 1/2012 |

OTHER PUBLICATIONS

NIST Chemistry WebBook, SRD 69, "N-formylmorpholine" via https://webbook.nist.gov/cgi/cbook.cgi?ID=4394-85-8, pp. 1-2 (2021).
International Search Report issued Oct. 14, 2019 for PCT/EP2018/083683, Dec. 5, 2018.

* cited by examiner

COMPOSITION AND PROCESS FOR SELECTIVELY ETCHING A LAYER COMPRISING AN ALUMINIUM COMPOUND IN THE PRESENCE OF LAYERS OF LOW-K MATERIALS, COPPER AND/OR COBALT

CROSS-REFERENCE TO RELATED APPLICATIONS

This application is a continuation application of U.S. patent application Ser. No. 16/765,371, filed May 19, 2020, which is a U.S. National Phase Application of International Patent Application No. PCT/EP18/83683, filed Dec. 5, 2018, which claims priority to EP Patent Application No. 18180361.0, filed Jun. 28, 2018, and which claims priority to EP Patent Application No. 17206096.4, filed Dec. 8, 2017, each of which is hereby incorporated by reference herein.

The present invention relates to a composition for selectively etching a layer comprising an aluminium compound in the presence of a layer of a low-k material and/or a layer comprising copper and/or cobalt, and to a corresponding use of said composition. The present invention further relates to a process for the manufacture of a semiconductor device, comprising the step of selectively etching at least one layer comprising an aluminium compound in the presence of a layer of a low-k material and/or a layer comprising copper and/or cobalt, by contacting the at least one layer comprising an aluminium compound with said composition.

Processes for manufacturing semiconductor devices are multiple-step sequences of photolithographic and chemical processing steps during which electronic circuits are gradually created on a wafer made of pure semiconducting material (a "semiconductor wafer"). Preferably, silicon is used as the semiconductor material. A typical semiconductor wafer is made out of extremely pure silicon that is grown into mono-crystalline cylindrical ingots (boules) up to 300 mm in diameter using the so-called "Czochralski process". These ingots are then sliced into wafers about 0.75 mm thick and polished to obtain a very regular and flat surface.

The particular process for manufacturing semiconductor wafers is structured in several phases, comprising e.g. the so-called "front-end-of-line" ("FEOL") and "back-end-of-line" ("BEOL") processing phases.

The FEOL processing phase refers to the formation of transistors directly in the material (usually the silicon) of the semiconductor wafer. The raw semiconductor wafer is engineered by the growth of an ultrapure, virtually defect-free silicon layer through epitaxy.

Front-end surface engineering is followed by growth of the gate dielectric (e.g. silicon dioxide), patterning of the gate, patterning of the source and drain regions, and subsequent implantation or diffusion of dopants into the semiconducting material to obtain the desired complementary electrical properties.

Once the various devices (e.g. dynamic random access memories, DRAMs; static random access memories, SRAMs; electrically programmable read only memories, EPROMs; or complementary metal on silicon, CMOS) have been created in FEOL processing, they must be interconnected to form the desired electrical circuits. This occurs in a series of wafer processing steps collectively referred to as BEOL. The BEOL processing phase involves creating metal interconnecting wires on the semiconductor wafer's surface that are isolated by layers made of material with low dielectric constant, e.g. a material which has a dielectric constant κ<3.9 (also known as a "low-k material"). With the introduction of copper (Cu) as electrically conductive material instead of aluminium, sophisticated multiple-step manufacturing processes for forming Integrated Circuit (IC) interconnects on semiconductor substrates have been developed, comprising various methods for selectively creating and removing consecutive layers of electrically conductive and of insulating (dielectric) materials, e.g. using chemical vapour deposition (CVD), electroplating, photolithography, wet etching or dry etching techniques, chemical-mechanical polishing (CMP), as well as several cleaning steps, e.g. to remove residues from previous material removing steps from the surface of a processed semiconductor substrate. Recently, also cobalt metal has attracted much interest in the semiconductor industry, e.g. for use in barrier layers or in seed layers and/or for encapsulating copper interconnects, to improve processes for manufacturing semiconductor devices.

One such multiple-step manufacturing process is known as damascene manufacturing process with its variants like the dual damascene process, including the TFVL ("trench-first-via-last") dual damascene process, the VFTL ("via-first-trench-last") dual damascene process, the self-aligned dual damascene process or the dual damascene patterning process with metal hard mask (for the latter see e.g. document U.S. Pat. No. 6,696,222).

In the damascene processing technology, the desired IC interconnect structure is patterned by etching the shape of the structure into the underlying inter-layer dielectric ("ILD") materials. After the patterning, typically a thin barrier layer (e.g. made of Ta/TaN, TiN, CoWP, NiMoP or NiMoB) is deposited on top of the etched structure as copper diffusion barrier. On top of that barrier layer a seed layer is often deposited which supports better adhesion of the copper on the underlying material and acts as catalytic material during the plating process as well. Typical materials for these seed layers are compounds which include Pd, Co, or other compounds, e.g. of polymers and organic materials. The original deposition process (damascene process) was designed to process each layer on its own. Hence, the so called "vertical interconnect accesses" ("vias") and the metallization levels have different process steps and demand a sequence of cleaning, material deposition, CMP, and another cleaning step for each layer. A copper technology using this sequence for its metallization levels as well as for its ILDs and inter via dielectrics ("IVD"s) is often called a "single damascene process". Typically, in the single damascene process each level requires its own cap layer or etch-stop layer, a separate ILD layer, and at the top there is a need for a material—for instance $SiO_2$—that can be polished together with the interconnect metal copper. Alternatively, the dual damascene processing technology combines certain similar process steps to one single process step, thus reducing the number of process steps and the time and costs required to build the BEOL stack. Hence the dual damascene process fabricates the IVD and the metallization layer at once.

In said damascene manufacturing process or its variants, electrically conductive masks (or "hard masks") are often used to protect one or more subjacent layers, e.g. subjacent layers of dielectric material like of low-k material during certain etch steps. Such electrically conductive ("metal") masks (or "hard masks") are usually deposited in the form of a layer comprising e.g. Ti, TiN, Ta, TaN, Al, $HfO_x$ (i.e. hafnium oxide) or AlCu. For example, in the dual damascene patterning process with metal hard mask a metallic layer deposited on the dielectric (low-k) material serves as hard mask for a second etch step.

With the ongoing requirement to further minimize the structures on a semiconductor wafer, manufacturers are facing new challenges: for example, in integration schemes for further minimized structures on semiconductor wafers like in integration schemes for manufacturing 20 nm structures or sub-20 nm structures or for manufacturing 10 nm structures or sub-10 nm structures on semiconductor wafers, via creation is preferably done by using a metal hard mask, often a TiN hard mask, and a subsequent dry etch step to remove the low-k material which is situated underneath the metal (e.g. TiN) hard mask (and is optionally separated from the metal/TiN hardmask by an additional layer, e.g. a non-metal hard mask or a bonding layer). In order to protect the underlying copper and/or cobalt at the bottom of the via to be created, a thin etch-stop layer is usually deposited on the copper and/or cobalt (i.e. on the copper and/or cobalt metal's surface). This thin etch-stop layer often comprises or consists of an aluminium compound and can have a maximum thickness of 30 nm or below, in particular of 20 nm or below, more in particular of 10 nm or below or even of 5 nm or below.

In order to proceed with the manufacturing process, the following materials have to be removed: 1) the metal (e.g. TiN) hard mask, 2) any polymeric residues still in the via; and 3) the etch-stop layer. Simultaneously, materials such as the low-k material, the copper metal and/or the cobalt metal should not be etched. This threefold removal of material—while at the same time preserving to the highest extent possible the layer of low-k material, the copper metal and/or the cobalt metal—can be achieved by either a 1-step process or a 2-step process.

In said 1-step process all of said three removal steps are performed simultaneously by applying a suitable composition which usually comprises an oxidation agent like hydrogen peroxide.

In said 2-step process, in a first step, the metal (e.g. TiN) hard mask is removed, usually together with residues from previous production steps, e.g. polymeric residues, by applying a composition which usually comprises an oxidation agent like hydrogen peroxide. Said composition should not damage the layer of low-k material or the etch-stop layer, specifically the etch-stop layer comprising or consisting of an aluminium compound. In the second step, the etch-stop layer is to be removed by applying a suitable composition. Typically, in this second step the polymeric residues still in the via are also removed (see above).

The composition to be used in this second step should remove only the thin etch-stop layer, specifically the etch-stop layer comprising or consisting of an aluminium compound, and not—or only to the least possible extent—damage the layer of low-k material, the copper metal and/or the cobalt metal. For this purpose, the composition to be used in said second step needs to have properties which allow a very controlled and specific etching of layers comprising or consisting of an aluminium compound, even of thin or ultra-thin layers comprising or consisting of an aluminium compound, while not compromising layers of low-k materials, copper metal and/or cobalt metal, which may also be present. The compositions according to the present invention as defined in this text are therefore preferably applied in said second step of said 2-step process.

It has been known that dielectric films of aluminium oxide can generally be removed by wet etching in acidic and basic media (see e.g. B. Zhou et al., J. Electrochem. Soc. Vol. 143 (2) 619-623 (1996) or J. Oh et al. J. Electrochem. Soc. Vol. 156 (4) D217-D222 (2011)), however, not with the etch-rate precision and reliability required for etching thin or ultra-thin etch-stop layers comprising or consisting of an aluminium compound, e.g. aluminium oxide.

Document WO 03/035797 relates to an aqueous cleaning composition containing copper-specific corrosion inhibitor for cleaning inorganic residues on a semiconductor substrate.

Document WO 2012/009639 A2 relates to an aqueous cleaner for the removal of post-etch residues.

Document U.S. 2004/061092 relates to a wet etch for selective removal of alumina.

Document U.S. 2010/0075478 relates to a method for pattern resist removal.

Document WO 2009/064336 teaches compositions for removal of metal hard mask etching residues from a semiconductor substrate.

Document WO 2004/030038 A2 relates to compositions substrate for removing etching residue and use thereof.

Document U.S. 2012/0052686 relates to a cleaning solution and damascene processing using the same.

It was therefore a primary object of the present invention to provide a composition for selectively etching a layer of an aluminium compound in the presence of a layer of a low-k material and/or a layer comprising copper and/or cobalt, with properties which allow for a very controlled and specific etching, even of thin or ultra-thin layers of an aluminium compound, while at the same time not or not significantly compromising layers of low-k materials and/or layers comprising copper metal and/or cobalt metal, which are also present.

It was another specific object of the present invention to provide a process for manufacturing a semiconductor device wherein a layer of an aluminium compound is selectively etched in the presence of a low-k material, of copper metal and/or of cobalt metal. Further objects of the present invention are disclosed in or become apparent from the present description and the accompanying claims.

It has now been found that the primary object and other objects of the invention are accomplished by a composition for selectively etching a layer comprising an aluminium compound, preferably a layer comprising aluminium oxide, in the presence of a layer of a low-k material and/or a layer comprising copper and/or cobalt, the composition comprising (i.e. one or more further substances may be present):

(A) one or more solubilizers, selected from the group consisting of
a compound of formula I:

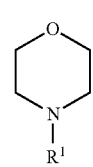

(I)

wherein $R^1$ is selected from the group consisting of
hydrogen and
—C(O)—$R^2$ wherein $R^2$ is selected from the group consisting of hydrogen and alkyl having 1, 2, 3 or 4 carbon atoms;

a compound of formula II:

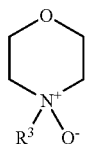

wherein R³ is alkyl having 1, 2, 3 or 4 carbon atoms;
trimethylamine-N-oxide,
triethylamine-N-oxide,
triethanolamine-N-oxide,
pyridine-N-oxide,
N-ethylpyrrolidine-N-oxide and
mixtures thereof;
(B) one or more etchants comprising fluoride anions; preferably selected from the group consisting of ammonium fluoride, ammonium bifluoride, triethanolammonium fluoride, diglycolammonium fluoride, methyldiethanolammonium fluoride, tetramethylammonium fluoride, triethylamine trihydrofluoride, hydrogen fluoride, fluoroboric acid, tetrafluoroboric acid, ammonium tetrafluoroborate, fluoroacetic acid, ammonium fluoroacetate, trifluoroacetic acid, fluorosilicic acid, ammonium fluorosilicate, tetrabutylammonium tetrafluoroborate and mixtures thereof;
(C) one or more corrosion inhibitors, selected from the group consisting of
benzotriazole which is unsubstituted or substituted once or twice independently by $C_{1-4}$-alkyl, amino-$C_{1-4}$-alkyl, phenyl, thiophenyl, halogen, hydroxy, nitro and/or thiol;
ethylene urea, ethylene thiourea, 1,2,4-triazole, 5-aminotetrazole, 5-amino-1,3,4-thiadiazol-2-thiol, 3-amino-1H-1,2,4 triazole, 3,5-diamino-1,2,4-triazole, tolyltriazole, 3-amino-5-mercapto-1,2,4-triazole, 1-amino-1,2,4-triazole, 1-amino-1,2,3-triazole, 1-amino-5-methyl-1,2,3-triazole, 3-mercapto-1,2,4-triazole, 3-isopropyl-1,2,4-triazole, naphthotriazole, 1H-tetrazole-5-acetic acid, 1-phenyl-2-tetrazoline-5-thione, 4-methyl-2-phenylimidazole, 2-mercaptothiazoline, 2,4-diamino-6-methyl-1,3,5-triazine, thiazole, imidazole, benzimidazole, triazine, methyltetrazole, 1,3-dimethyl-2-imidazolidinone, 1,5-pentamethylenetetrazole, 1-phenyl-5-mercaptotetrazole, 2H-imidaz-ole-2-thione, 4-methyl-4H-1,2,4-triazole-3-thiol, 5-amino-1,3,4-thiadiazole-2-thiol, benzothiazole, tritolyl phosphate, indazole, adenine, cytosine, guanine, thymine, 2,2'-azanediyldiacetic acid, propanethiol, citric acid, ascorbic acid, thiourea, 1,1,3,3-tetramethylurea, urea, uric acid, glycine, dodecylphosphonic acid, oxalic acid, malonic acid, succinic acid, nitrilotriacetic acid and mixtures thereof;
(D) one or more chelating agents selected from the group consisting of histidine, preferably L-histidine; 1,2-cyclohexylenedinitrilotetraacetic acid, 1,1,1,5,5,5-hexafluoro-2,4-pentanedione, acetylacetonate, 2,2'-azanediyldiacetic acid, ethylenediaminetetraacetic acid, etidronic acid, methanesulfonic acid, acetylacetone, 1,1,1-trifluoro-2,4-pentanedione, 1,4-benzoquinone, 8-hydroxyquinoline, salicylidene aniline; tetrachloro-1,4-benzoquinone, 2-(2-hydroxyphenyl)-benzoxazol, 2-(2-hydroxyphenyl)-benzothiazole, hydroxyquinoline sulfonic acid, sulfosalicylic acid, salicylic acid, pyridine, 2-ethylpyridine, 2-methoxypyridine, 3-methoxypyridine, 2-picoline, dimethylpyridine, piperidine, piperazine, triethylamine, triethanolamine, ethylamine, methylamine, isobutylamine, tert-butylamine, tributylamine, dipropylamine, dimethylamine, diglycol amine, monoethanolamine, methyldiethanolamine, pyrrole, isoxazole, bipyridine, pyrimidine, pyrazine, pyridazine, quinoline, isoquinoline, indole, 1-methylimidazole, diisopropylamine, diisobutylamine, aniline, pentamethyldiethylenetriamine, acetoacetamide, ammonium carbamate, ammonium pyrrolidinedithiocarbamate, dimethyl malonate, methyl acetoacetate, N-methyl acetoacetamide, tetramethylammonium thiobenzoate, 2,2,6,6-tetramethyl-3,5-heptanedione, tetramethylthiuram disulfide, lactic acid, ammonium lactate, formic acid, propionic acid, gammabutyrolactone, and mixtures thereof;
and
(G) water.

It was particularly surprising that the composition according to the invention is suited to allow for a very controlled and specific etching of layers comprising or consisting of an aluminium compound, even of thin or ultra-thin layers comprising or consisting of an aluminium compound, while at the same time not or not significantly compromising layers of low-k materials, of copper metal and/or of cobalt metal which are also present.

The invention as well as preferred embodiments and preferred combinations of parameters, properties and elements thereof are defined in the appended claims. Preferred aspects, details, modifications and advantages of the present invention are also defined and explained in the following description and in the examples stated below.

In the context of the present invention, an "aluminium compound" comprises one or more compounds selected from the group consisting of aluminium oxide ("$AlO_x$"), aluminium nitride, aluminium oxynitride ("AlON") and aluminium carbooxynitride ("AlCNO"). Preferably, an aluminium compound also comprises fluorine. The exact composition of an aluminium compound and the exact contents or ratios of the elements aluminium, oxygen, nitrogen, carbon and/or fluorine present in an aluminium compound as defined herein can vary, e.g. depending on the kind of pre-treatment of a semiconductor device comprising said aluminium compound.

In the context of the present invention, a "layer comprising or consisting of an aluminium compound" preferably means an etch-stop layer, more preferably an etch-stop layer deposited on a copper layer and/or a cobalt layer, preferably on a copper layer or a cobalt layer.

An etch-stop layer as referred to herein is—consistent with the usual meaning in the field—a layer of a material that is not etched under the conditions applied in usual etching processes for structuring the surface of a microelectronic device, in particular a semiconductor wafer, and which covers and thereby protects subjacent materials which are potentially sensitive to said etching processes, e.g. copper or other metals like copper interconnects, from undesired attacks of the etching agents applied. After the etching process, the etch-stop layer can be removed under conditions specific to the material of the etch-stop layer which removal also will not negatively affect the subjacent materials.

In the context of the present invention, a "low-k material" preferably is a material with a dielectric constant κ<3.9 and/or (preferably "and")
is selected from the group consisting of (i) silicon-containing materials, preferably selected from the group consisting of $SiO_2$, silicon oxycarbide (SiOC), tetraethylorthosilicate (TEOS), boron-doped phosphosilicate glass (BPSG), fluorine-doped silicon dioxide (fluorosilicate glass, FSG), carbon-doped silicon dioxide, organo silicate glass (OSG), carbon-doped oxide (CDO), porous silicon dioxide, porous carbon-doped silicon-dioxide and spin-on silicon polymeric materials, preferably hydrogen silsesquioxane (HSQ) and methylsilsesquioxane (MSQ); preferably organic siloxanes (i.e. siloxanes comprising carbon-silicon bonds); and preferably organic silanes (i.e. silanes comprising carbon-silicon bonds) and (ii) polymeric materials, preferably selected from the group consisting of spin-on organic polymeric dielectrics, preferably comprising polyimide (PI); polynorbornenes; benzocyclobutene and polytetrafluorethylene (PTFE).

In the context of the present invention, the term "selectively etching" (or "selective etch rate") preferably means that upon applying a composition according to the invention to a layer comprising or consisting of an aluminium compound in the presence of a layer of a low-k material and/or a layer comprising copper and/or cobalt, preferably a layer comprising copper, the etch rate of said composition for etching the layer comprising or consisting of an aluminium compound, preferably of aluminium oxide, is at least 10 times, preferably at least 100 times, the etch rate of said composition for said low-k material and/or for said layer comprising copper and/or cobalt, preferably for said layer comprising copper.

In the context of the present invention, the term "selectively etching in the presence of a cobalt layer" (or "selective etch rate in the presence of a cobalt layer" or equivalent expressions) preferably means that upon applying a composition according to the invention to a layer comprising or consisting of an aluminium compound in the presence of a layer of a low-k material and/or a layer comprising cobalt, the etch rate of said composition for etching the layer comprising or consisting of an aluminium compound, preferably of aluminium oxide, is at least 2 times, preferably at least 3 times, the etch rate of said composition for said low-k material and/or for said layer comprising cobalt. As is known in the field, cobalt or a layer comprising cobalt is usually more sensitive to etching processes of the type described or referred to herein than copper or a layer comprising copper.

In the composition according to the invention as defined above (all variants), the one or more solubilizers (A), the one or more etchants comprising fluoride anions (B), the one or more corrosion inhibitors (C) and the one or more chelating agents (D) generally can in each case be used alone (as one single compound) or can be used in combination with other compounds of the same type (solubilizer, etchant, corrosion inhibitor or chelating agent, respectively, as applicable).

In component (A), where the one or more solubilizers of the composition according to the invention comprise a compound of formula I, $R^1$ is preferably a group —C(O)—$R^2$ wherein $R^2$ is selected from the group consisting of hydrogen and alkyl having 1, 2, 3 or 4 carbon atoms. Where $R^2$ is alkyl having 1, 2, 3 or 4 carbon atoms, this comprises methyl, ethyl and branched and unbranched propyl and butyl. Preferably, $R^2$ is hydrogen. N-formylmorpholine (CAS RN 4394-85-8, also referred to as "NFM" in this text) is a particularly preferred compound of formula I for use in the composition according to the invention.

In component (A) where the one or more solubilizers of the composition according to the invention comprise a compound of formula II, $R^3$ comprises methyl, ethyl and branched and unbranched propyl and butyl. Preferably, $R^3$ is methyl. 4-methylmorpholine-4-oxide (also referred to as "4-MM-4-O" in this text and also known as N-methylmorpholine-N-oxide, CAS RN 7529-22-8) is a particularly preferred compound of formula II for use in the composition according to the invention. The present definition of the compound of formula II includes hydrates, specifically the monohydrate of 4-methylmorpholine-4-oxide (CAS RN 70187-32-5), isomers and tautomers of compounds of formula II.

In component (B) of the composition according to the invention (all variants), the one or more etchants comprising fluoride anions can comprise one or more fluoride anions or provide one or more fluoride anions upon contact with water. A composition according to the invention as defined herein (or a composition according to the invention as described above or below as being preferred) is thus preferred wherein the or at least one component (B) is selected from the group consisting of ammonium fluoride, ammonium bifluoride, triethanolammonium fluoride, diglycolammonium fluoride, methyldiethanolammonium fluoride, tetramethylammonium fluoride, triethylamine trihydrofluoride, hydrogen fluoride, fluoroboric acid, tetrafluoroboric acid, ammonium tetrafluoroborate, fluoroacetic acid, ammonium fluoroacetate, trifluoroacetic acid, fluorosilicic acid, ammonium fluorosilicate, tetrabutylammonium tetrafluoroborate and mixtures thereof; and preferably the or at least one component (B) is ammonium fluoride (CAS RN 12125-01-8) and wherein component (B) more preferably is ammonium fluoride.

Compositions according to the invention comprising ammonium fluoride as component (B) have shown a stable and reproducible controlled (selective) etch rate for etching a layer comprising or consisting of an aluminium compound, in particular of aluminium oxide, in the presence of a layer of a low-k material and/or a layer comprising copper and/or cobalt.

Where component (C) comprises benzotriazole which is unsubstituted or substituted (as defined above) this definition comprises one such benzotriazole and a plurality of such benzotriazoles which can independently be unsusbstituted or substituted as defined above, and includes mixtures of such benzotriazoles.

Where component (C) comprises benzotriazole which is substituted once or twice independently by $C_{1-4}$-alkyl or amino-$C_{1-4}$-alkyl, "$C_{1-4}$-alkyl" means alkyl having 1, 2, 3 or 4 carbon atoms and comprises methyl, ethyl and branched and unbranched propyl and butyl. Where component (C) comprises benzotriazole which is substituted by $C_{1-4}$-alkyl, methyl is preferred. Specific compounds which are comprised by the present definition are 5-methylbenzotriazole and 6-methylbenzotriazole (for applicable nomenclature see below). Where component (C) comprises benzotriazole which is substituted by amino-$C_{1-4}$-alkyl, 2-(5-amino-pentyl) is preferred.

Where component (C) comprises benzotriazole which is substituted once or twice independently by halogen, said halogen is selected from fluorine, chlorine, bromine and iodine. Benzotriazole substituted by chlorine, preferably substituted once by chlorine, is preferred. Where component (C) comprises benzotriazole which is substituted by halogen (preferably as defined here before), this is also referred to as "halobenzotriazole" in this text.

Where component (C) comprises benzotriazole which is unsubstituted or substituted once or twice independently by $C_{1-4}$-alkyl, amino-$C_{1-4}$-alkyl, phenyl, thiophenyl, halogen, hydroxy, nitro and/or thiol this definition specifically comprises the compounds benzotriazole, 6-methyl-benzotriazole (6-Me-BTA), 5-methyl-benzotriazole (5-Me-BTA), 1-hydroxybenzotriazole, 5-phenyl-benzotriazole, 5-nitro-benzotriazole, 2-(5-amino-pentyl)-benzotriazole, 5-phenylthiolbenzotriazole, halobenzotriazoles (where halo is selected from the group consisting of F, Cl, Br and I) and 2-mercaptobenzothiazole.

As is known in the technical field, in benzotriazoles the bond between positions (i.e. ring nitrogen atoms) 1 and 2 and the bond between positions (i.e. ring nitrogen atoms) 2 and 3 have proved to have the same bond properties. The proton attached to one nitrogen atom in the nitrogen-containing ring of the benzotriazole structure does not tightly bind to any of the three ring nitrogen atoms present but rather migrates rapidly between positions 1 and 3, thus creating tautomers.

For the purposes of the present invention, the name "5-methyl-2H-benzotriazole" as used above therefore comprises this compound and all tautomers thereof, specifically the compounds known as "5-methyl-benzotriazole", "6-methyl-benzotriazole" (CAS RN 49636-02-4), "6-methyl-1H-benzo[d][1.2.3]triazole", "5-methyl-1H-benzo[d][1.2.3]triazole" and "5-methyl-2H-benzo[d][1.2.3]triazole". And vice versa a compound referred to in the present text as "5-methyl-2H-benzotriazole", "5-methyl-benzotriazole", "6-methyl-benzotriazole", "6-methyl-1H-benzo[d][1.2.3]triazole", "5-methyl-1H-benzo[d][1.2.3]triazole", "5-methyl-2H-benzo[d][1.2.3]triazole", "5-Me-BTA" or "6-Me-BTA" in each case has the same meaning as the compound "5-methyl-2H-benzotriazole and all of its tautomers".

Correspondingly, for the purposes of the present invention, the name "5-chloro-2H-ben-zotriazole" as used in the present text comprises this compound and all tautomers thereof, specifically the compounds known as "5-chloro-benzotriazole" (CAS RN 94-97-3), "6-chloro-benzotriazole", "6-chloro-1H-benzo[d][1.2.3]triazole", "5-chloro-1H-benzo[d][1.2.3]-triazole" and "5-chloro-2H-benzo[d][1.2.3]triazole". And vice versa a compound referred to in the present text as "5-chloro-2H-benzotriazole", "5-chloro-benzotriazole", "6-chloro-benzotriazole", "6-chloro-1H-benzo[d][1.2.3]triazole", "5-chloro-1H-benzo[d][1.2.3]triazole", "5-chloro-2H-benzo[d][1.2.3]triazole", "5-Cl-BTA" or "6-Cl-BTA" in each case has the same meaning as the compound "5-chloro-2H-benzotriazole and all of its tautomers". This definition applies mutatis mutandis to other benzotriazoles, in particular substituted benzotriazoles, as defined or mentioned in the present text.

Benzotriazole which is unsubstituted or substituted once or twice, preferably once, independently by $C_{1-4}$-alkyl, preferably methyl, and/or (preferably "or") halogen is preferred. In a particularly preferred variant of the present invention, component (C) is selected from the group consisting of unsubstituted benzotriazole (BTA), 5-methyl-2H-benzotriazole, 5-chloro-2H-benzotriazole and mixtures thereof.

A composition according to the invention as defined herein (or a composition according to the invention as described above or below as being preferred) is preferred
wherein
the or at least one component (A) is selected from the group consisting of
a compound of formula I as defined above (or a preferred compound of formula I as defined above),
and
a compound of formula II as defined above (or a preferred compound of formula II as defined above),
and/or
component (B) is selected from the group consisting of ammonium fluoride, ammonium bifluoride, triethanolammonium fluoride, diglycolammonium fluoride, methyldiethanolammonium fluoride, tetramethylammonium fluoride, triethylamine trihydrofluoride, hydrogen fluoride, fluoroboric acid, tetrafluoroboric acid, ammonium tetrafluoroborate, fluoroacetic acid, ammonium fluoroacetate, trifluoroacetic acid, fluorosilicic acid, ammonium fluorosilicate, tetrabutylammonium tetrafluoroborate and mixtures thereof;
and preferably the or at least one component (B) is ammonium fluoride and more preferably component (B) is ammonium fluoride,
and/or
the or at least one component (C) is selected from the group consisting of
benzotriazole which is unsubstituted or substituted once or twice, preferably once, independently by $C_{1-4}$-alkyl, amino-$C_{1-4}$-alkyl, phenyl; thiophenyl; halogen, hydroxy, nitro and/or (preferably "or") thiol;
preferably benzotriazole which is unsubstituted or substituted once or twice, preferably once, independently by $C_{1-4}$-alkyl and/or (preferably "or") halogen,
succinic acid
and
mixtures thereof.

A composition according to the invention as defined herein (or a composition according to the invention as described above or below as being preferred) is also preferred
wherein
the or at least one component (D) is selected from the group consisting of histidine, preferably L-histidine; 1,2-cyclohexylenedinitrilotetraacetic acid, and mixtures thereof,
and/or
the composition comprises as further component:
(E) one or more surfactants.

In the compositions according to the invention as defined above, the one or more surfactants (E) generally (if present) can in each case be used alone (as one single compound) or can be used in combination with other compounds of the same type.

Further preferred is a composition according to the invention as defined herein (or a composition according to the invention as described above or below as being preferred)
wherein
the pH of the composition is in the range of from 3.5 to 8,
and/or
the composition comprises as further component:
(F) a buffering system which is suitable to buffer the pH of the composition in the range of from 3.5 to 8.

Also preferred is a composition according to the invention as defined herein (or a composition according to the invention as described above or below as being preferred) comprising (i.e. one or more further substances may be present):
- (A) one or more solubilizers selected from the group consisting of
    - a compound of formula I as defined above (or a preferred compound of formula I as defined above), and
    - a compound of formula II as defined above (or a preferred compound of formula II as defined above),
- (B) one or more etchants, selected from the group consisting of ammonium fluoride, ammonium bifluoride, triethanolammonium fluoride, diglycolammonium fluoride, methyldiethanolammonium fluoride, tetramethylammonium fluoride, triethylamine trihydrofluoride, hydrogen fluoride, fluoroboric acid, tetrafluoroboric acid, ammonium tetrafluoroborate, fluoroacetic acid, ammonium fluoroacetate, trifluoroacetic acid, fluorosilicic acid, ammonium fluorosilicate, tetra butylammonium tetrafluoroborate and mixtures thereof;
    - wherein preferably the or at least one etchant component (B) is ammonium fluoride and more preferably etchant component (B) is ammonium fluoride;
- (C) one or more corrosion inhibitors, selected from the group consisting of
    - benzotriazole which is unsubstituted or substituted once or twice, preferably once, independently by $C_{1-4}$-alkyl, amino-$C_{1-4}$-alkyl, phenyl, thiophenyl, halogen, hydroxy, nitro and/or (preferably "or") thiol;
        - preferably benzotriazole which is unsubstituted or substituted once or twice, preferably once, independently by $C_{1-4}$-alkyl and/or (preferably "or") halogen,
    - succinic acid
    and
    - mixtures thereof,
- (D) one or more chelating agents selected from the group consisting of histidine, 1,2-cyclohexylenedinitrilotetraacetic acid and mixtures thereof
- (G) water,
wherein the pH of the composition is in the range of from 3.5 to 8.

In a first preferred variant, the composition according to the present invention pertains to a composition for selectively etching a layer comprising an aluminium compound, preferably a layer comprising aluminium oxide, in the presence of a layer of a low-k material and/or a layer comprising copper and/or cobalt, preferably in the presence of a low-k material and/or a copper layer, the composition comprising (i.e. one or more further substances may be present) or consisting of (i.e. no further substances are present in addition to component (A) to (G) as defined hereinafter)
- (A) one or more solubilizers, selected from the group consisting of 4-methylmorpholine-4-oxide, trimethylamine-N-oxide, triethylamine-N-oxide, triethanolamine-N-oxide, pyridine-N-oxide, N-ethylmorpholine-N-oxide, N-ethylpyrrolidine-N-oxide and mixtures thereof;
- (B) one or more etchants comprising fluoride anions, preferably selected from the group consisting of ammonium fluoride, ammonium bifluoride, triethanolammonium fluoride, diglycolammonium fluoride, methyldiethanolammonium fluoride, tetramethylammonium fluoride, triethylamine trihydrofluoride, hydrogen fluoride, fluoroboric acid, tetrafluoroboric acid, ammonium tetrafluoroborate, fluoroacetic acid, ammonium fluoroacetate, trifluoroacetic acid, fluorosilicic acid, ammonium fluorosilicate, tetrabutylammonium tetrafluoroborate and mixtures thereof;
- (C) one or more corrosion inhibitors, selected from the group consisting of benzotriazole, (6-methyl-benzotriazole (6-Me-BTA)), 5-methyl-benzotriazole, ethylene urea, ethylene thiourea, 1,2,4-triazole, 5-aminotetrazole, 1-hydroxybenzotriazole, 5-amino-1,3,4-thiadiazol-2-thiol, 3-amino-1H-1,2,4 triazole, 3,5-diamino-1,2,4-triazole, tolyltriazole, 5-phenyl-benzotriazole, 5-nitro-benzotriazole, 3-amino-5-mercapto-1,2,4-triazole, 1-amino-1,2,4-triazole, 2-(5-amino-pentyl)-benzotriazole, 1-amino-1,2,3-triazole, 1-amino-5-methyl-1,2,3-triazole, 3-mercapto-1,2,4-triazole, 3-isopropyl-1,2,4-triazole, 5-phenylthiol-benzotriazole, halobenzotriazoles (where halo is selected from the group consisting of F, Cl, Br and I), naphthotriazole, 1H-tetrazole-5-acetic acid, 2-mercaptobenzothiazole, 1-phenyl-2-tetrazoline-5-thione, 2-mercaptobenzimidazole, 4-methyl-2-phenylimidazole, 2-mercaptothiazoline, 2,4-diamino-6-methyl1,3,5-triazine, thiazole, imidazole, benzimidazole, triazine, methyltetrazole, 1,3-dimethyl-2-imidazolidinone, 1,5-pentamethylenetetrazole, 1-phenyl-5-mercaptotetrazole, 2H-imidazole-2-thione, 4-methyl-4H-1,2,4-triazole-3-thiol, 5-amino-1,3,4-thiadiazole-2-thiol, benzothiazole, tritolyl phosphate, indazole, adenine, cytosine, guanine, thymine, 2,2'-azanediyldiacetic acid, propanethiol, citric acid, ascorbic acid, thiourea, 1,1,3,3-tetramethylurea, urea, uric acid, glycine, dodecylphosphonic acid, oxalic acid, malonic acid, succinic acid, nitrilotriacetic acid and mixtures thereof;
- (D) one or more chelating agents selected from the group consisting of 1,2-cyclohexylenedinitrilotetraacetic acid, 1,1,1,5,5,5-hexafluoro-2,4-pentanedione, acetylacetonate, 2,2'-azanediyldiacetic acid, ethylenediaminetetraacetic acid, etidronic acid, methanesulfonic acid, acetylacetone, 1,1,1-trifluoro-2,4-pentanedione, 1,4-benzoquinone, 8-hydroxyquinoline, salicylidene aniline; tetrachloro-1,4-benzoquinone, 2-(2-hydroxyphenyl)-benzoxazol, 2-(2-hydroxyphenyl)-benzothiazole, hydroxyquinoline sulfonic acid, sulfosalicylic acid, salicylic acid, pyridine, 2-ethylpyridine, 2-methoxypyridine, 3-methoxypyridine, 2-picoline, dimethylpyridine, piperidine, piperazine, triethylamine, triethanolamine, ethylamine, methylamine, isobutylamine, tert-butylamine, tributylamine, dipropylamine, dimethylamine, diglycol amine, monoethanolamine, methyldiethanolamine, pyrrole, isoxazole, bipyridine, pyrimidine, pyrazine, pyridazine, quinoline, isoquinoline, indole, 1-methylimidazole, diisopropylamine, diisobutylamine, aniline, pentamethyldiethylenetriamine, acetoacetamide, ammonium carbamate, ammonium pyrrolidinedithiocarbamate, dimethyl malonate, methyl acetoacetate, N-methyl acetoacetamide, tetramethylammonium thiobenzoate, 2,2,6,6-tetramethyl-3,5-heptanedione, tetramethylthiuram disulfide, lactic acid, ammonium lactate, formic acid, propionic acid, gamma-butyrolactone, and mixtures thereof;
- (E) one or more surfactants;
- (F) a buffering system which is suitable to buffer the pH of the composition in the range of from 6 to 8, preferably in the range of from 6.4 to 7.5, and
- (G) water,
    wherein the pH of the composition is in the range of from 6 to 8, preferably in the range of from 6.4 to 7.5.

In the compositions according to the invention as defined above, specifically in the composition according to the invention according to the first preferred variant, the one or more solubilizers (A), the one or more etchants comprising fluoride anions (B), the one or more corrosion inhibitors (C), the one or more chelating agents (D) and the one or more surfactants (E) generally can in each case be used alone (as one single compound) or can be used in combination with other compounds of the same type (solubilizer, etchant, corrosion inhibitor, chelating agent or surfactant, respectively, as applicable).

Preferred is a composition according to the first preferred variant of the invention as defined herein, wherein
  the buffering system (F) is selected from the group consisting of a phosphate buffer comprising $NaH_2PO_4$ and $Na_2HPO_4$, a HEPES buffer comprising 2-[4-(2-hydroxyethyppiperazin-1-yl]ethanesulfonic acid, a TRIS buffer comprising tris(hydroxymethyl)-aminomethane, an ammonium acetate buffer and mixtures thereof,
    more preferably the buffering system is or comprises an ammonium acetate buffer and most preferably is an ammonium acetate buffer,
  and/or
  the pH of the composition is in the range of from 6.4 to 7.5, preferably in the range of from 6.8 to 7.5, more preferably in the range of from 7.0 to 7.4.

In the above-defined preferred composition according to the first preferred variant of the invention, the use of a single buffering system (e.g. just an ammonium acetate buffer or just a HEPES buffer) is preferred over the use of a mixture of buffering systems. All of said buffers as defined here above are known in the art and a skilled person will be aware how to apply and adjust said buffers in the context of the present invention. Compositions according to the invention with a pH in the range of from 6.4 to 7.5, preferably in the range of from 6.8 to 7.5, more preferably in the range of from 7.0 to 7.4 have shown a particularly stable and reproducible controlled (selective) etch rate for etching a layer comprising or consisting of an aluminium compound, preferably of aluminium oxide, in the presence of a layer of a low-k material and/or a layer comprising copper and/or cobalt, preferably in the presence of a low-k material and/or a copper layer. In addition, the aforementioned compositions according to the invention have shown to be particularly stable, e.g. storage-stable over a period of 6 months.

A composition according to the first preferred variant of the invention as defined herein (or a composition according to the first preferred variant of the invention as described above or below as being preferred) is preferred wherein the or at least one component (A) is 4-methylmorpholine-4-oxide (CAS RN 7529-22-8) and wherein preferably component (A) is 4-methylmorpholine-4-oxide.

Compositions according to the first preferred variant of the invention comprising 4-methyl-morpholine-4-oxide as component (A) have shown a stable and reproducible selective etch rate for etching a layer comprising or consisting of an aluminium compound, in particular of aluminium oxide, in the presence of a layer of a low-k material and/or a layer comprising copper and/or cobalt, in particular in the presence of a layer of a low-k material and/or a copper layer.

Compositions according to the first preferred variant of the invention comprising ammonium fluoride as component (B) have shown a stable and reproducible controlled (selective) etch rate for etching a layer comprising or consisting of an aluminium compound, in particular of aluminium oxide, in the presence of a layer of a low-k material and/or a layer comprising copper and/or cobalt, in particular in the presence of a layer of a low-k material and/or a copper layer.

A composition according to the first preferred variant of the invention as defined herein (or a composition according to the first preferred variant of the invention as described above or below as being preferred) is also preferred wherein component (C) is selected from the group consisting of benzotriazole (CAS RN 95-14-7), 6-methyl-benzotriazole (CAS RN 136-85-6) and a combination (i.e. a mixture) of benzotriazole and 6-methyl-benzotriazole, and preferably component (C) is a combination of benzotriazole and 6-methyl-benzotriazole. Compositions according to the first preferred variant of the invention comprising benzotriazole, 6-methyl-benzotriazole and a combination of benzotriazole and 6-methyl-benzotriazole as component (C), preferably comprising a combination of benzotriazole and 6-methyl-benzotriazole as component (C), have shown to be associated with a preferred particularly low copper etch rate. For nomenclature of unsubstituted and substituted benzotriazoles also see above.

A composition according to the first preferred variant of the invention as defined herein (or a composition according to the first preferred variant of the invention as described above or below as being preferred) is also preferred wherein component (D) is 1,2-cyclohexylene-dinitrilotetraacetic acid (CDTA; CAS RN 13291-61-7) or comprises CDTA as well as one or more of the other chelating agents above. Compositions according to the first preferred variant of the invention comprising CDTA as component (D) have shown a stable and reproducible controlled (selective) etch rate for etching a layer comprising or consisting of an aluminium compound, in particular of aluminium oxide, in the presence of a layer of a low-k material and/or a layer comprising copper and/or cobalt, in particular in the presence of a layer of a low-k material and/or a copper layer: said etch rate on semiconductor wafers was found to be uniform over a single wafer, with few or no centre-edge effects, and between different wafers.

A composition according to the invention as defined herein (or a composition according to the invention as described above or below as being preferred), in particular a composition according to the first preferred variant of the invention as defined herein, is also preferred wherein the one or more surfactants (E) (if present) are selected from the group consisting of:
  (i) anionic surfactants, preferably selected from the group consisting of ammonium lauryl sulfate, fluorosurfactants, preferably selected from the group consisting of perfluorinated alkylsulfonamide salts (preferably perfluorinated, N-substituted alkylsulfonamide ammonium salts, PNAAS), perfluorooctanesulfonate, perfluorobutanesulfonate, perfluorononanoate and perfluorooctanoate; alkyl-aryl ether phosphates and alkyl ether phosphates,
  (ii) zwitterionic surfactants, preferably selected from the group consisting of (3-[(3-cholamidopropyl)dimethyl-ammonio]-1-propanesulfonate) ("CHAPS"), cocamidopropyl hydroxysultaine (CAS RN 68139-30-0), {[3-(dodecanoylamino)propyl](dimethyl)ammonio}acetate, phosphatidylserine, phosphatidylethanolamine, phosphatidylcholine and
  (iii) non-ionic surfactants, preferably selected from the group consisting of glucoside alkyl ethers, glycerol alkyl ethers, cocamide ethanolamines and lauryldimethylaminoxide.

More preferred surfactants (E) in compositions according to the first preferred variant of the invention are or comprise perfluorinated, N-substituted alkylsulfonamide ammonium salts.

Preferred surfactants (E) in compositions according to the invention do not comprise metals or metal ions.

In individual cases, a composition according to the first preferred variant of the invention as defined herein (or a composition according to the first preferred variant of the invention as described above or below as being preferred) can further comprise as an optional additional component:
(H) one or more water-miscible organic solvents, preferably selected from the group consisting of tetrahydrofuran (THF), N-methylpyrrolidone (NMP), dimethyl formamide (DMF), dimethyl sulfoxide (DMSO), ethanol, isopropanol, butyldiglycol, butylglycol, sulfolane (2,3,4,5-tetrahydrothiophene-1,1-dioxide) and mixtures thereof; more preferably selected from the group consisting of THF, NMP, DMF, DMSO, sulfolane and mixtures thereof.

The term "water-miscible organic solvent" in the context of the present invention preferably means that an organic solvent fulfilling this requirement is miscible with water at least in a 1:1 (w/w) ratio at 20° C. and ambient (atmospheric) pressure. Preferably the or at least one water-miscible organic solvent (H) is sulfolane. More preferred are compositions according to the first preferred variant of the present invention which do not comprise one or more water-miscible organic solvents (H).

A composition according to the first preferred variant of the invention as defined herein is particularly preferred wherein one or more or all of the components (A), (B), (C), (D), (E) and (F) as defined above as being preferred are combined to result in a final (ready-to-use) composition according to the first preferred variant of the invention (comprising all components (A) to (G) or, in the less preferred case where component (H) is present, all components (A) to (H)).

In a second preferred variant, the composition according to the present invention pertains to a composition for selectively etching a layer comprising an aluminium compound, preferably a layer comprising aluminium oxide, in the presence of a layer of a low-k material and/or a layer comprising copper and/or cobalt, preferably in the presence of a low-k material and/or a cobalt layer, the composition comprising (i.e. one or more further substances may be present) or consisting of (i.e. no further substances are present in addition to component (A) to (D) and (G) as defined hereinafter):
(A) one or more solubilizers, selected from the group consisting of
a compound of formula I (with the preferred meanings of substituents $R^1$ and $R^2$ as defined above):

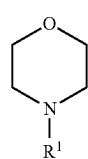

(I)

wherein $R^1$ is selected from the group consisting of hydrogen and

—C(O)—$R^2$ wherein $R^2$ is selected from the group consisting of hydrogen and alkyl having 1, 2, 3 or 4 carbon atoms;
a compound of formula II (with the preferred meanings of substituent $R^3$ as defined above):

(II)

wherein $R^3$ is alkyl having 1, 2, 3 or 4 carbon atoms;
trimethylamine-N-oxide
triethylamine-N-oxide,
triethanolamine-N-oxide,
pyridine-N-oxide,
N-ethylpyrrolidine-N-oxide and
mixtures thereof;
(B) one or more etchants comprising fluoride anions, preferably selected from the group consisting of ammonium fluoride, ammonium bifluoride, triethanolammonium fluoride, diglycolammonium fluoride, methyldiethanolammonium fluoride, tetramethylammonium fluoride, triethylamine trihydrofluoride, hydrogen fluoride, fluoroboric acid, tetrafluoroboric acid, ammonium tetrafluoroborate, fluoroacetic acid, ammonium fluoroacetate, trifluoroacetic acid, fluorosilicic acid, ammonium fluorosilicate, tetrabutylammonium tetrafluoroborate and mixtures thereof;
(C) one or more corrosion inhibitors, selected from the group consisting of
benzotriazole which is unsubstituted or substituted once or twice independently by $C_{1-4}$-alkyl, amino-$C_{1-4}$-alkyl, phenyl, thiophenyl, halogen, hydroxy, nitro and/or thiol;
ethylene urea, ethylene thiourea, 1,2,4-triazole, 5-aminotetrazole, 5-amino-1,3,4-thiadiazol-2-thiol, 3-amino-1H-1,2,4 triazole, 3,5-diamino-1,2,4-triazole, tolyltriazole, 3-amino-5-mercapto-1,2,4-triazole, 1-amino-1,2,4-triazole, 2-(5-amino-pentyl)-ben-zotriazole, 1-amino-1,2,3-triazole, 1-amino-5-methyl-1,2,3-triazole, 3-mercapto-1,2,4-triazole, 3-isopropyl-1,2,4-triazole, naphthotriazole, 1H-tetrazole-5-acetic acid, 1-phenyl-2-tetrazoline-5-thione, 4-methyl-2-phenylimidazole, 2-mercaptothiazoline, 2,4-diamino-6-methyl-1,3,5-triazine, thiazole, imidazole, benzimidazole, triazine, methyltetrazole, 1,3-dimethyl-2-imidazolidinone, 1,5-pentamethylenetetrazole, 1-phenyl-5-mercaptotetrazole, 2H-imidazole-2-thione, 4-methyl-4H-1,2,4-triazole-3-thiol, 5-amino-1,3,4-thiadiazole-2-thiol, benzothiazole, tritolyl phosphate, indazole, adenine, cytosine, guanine, thymine, 2,2'-azanediyldiacetic acid, propanethiol, citric acid, ascorbic acid, thiourea, 1,1,3,3-tetramethylurea, urea, uric acid, glycine, dodecylphosphonic acid, oxalic acid, malonic acid, succinic acid, nitrilotriacetic acid
and mixtures thereof;
(D) one or more chelating agents selected from the group consisting of histidine, preferably L-histidine; 1,2-cyclohexylenedinitrilotetraacetic acid, 1,1,1,5,5,5-hexafluoro-2,4-pentanedione, acetylacetonate, 2,2'-azanediyldiacetic acid, ethylenediaminetetraacetic acid, etidronic acid, methanesulfonic acid, acetylacetone, 1,1,1-trifluoro-2,4-pentanedione, 1,4-benzoquinone, 8-hydroxyquinoline, salicylidene aniline; tetrachloro-1,4-benzoquinone, 2-(2-hydroxyphenyl)-benzoxazol, 2-(2-hydroxyphenyl)-benzothiazole, hydroxyquinoline sulfonic acid, sulfosalicylic acid, salicylic acid, pyridine, 2-ethylpyridine, 2-methoxypyridine, 3-methoxypyridine, 2-picoline, dimethylpyridine, piperidine, piperazine, triethylamine, triethanolamine, ethylamine, methylamine, isobutylamine, tert-butylamine, tributylamine, dipropylamine, dimethylamine, diglycol amine, monoethanolamine, methyldiethanolamine, pyrrole, isoxazole, bipyridine, pyrimidine, pyrazine, pyridazine, quinoline, isoquinoline, indole, 1-methylimidazole, diisopropylamine, diisobutylamine, aniline, pentamethyldiethylenetriamine, acetoacetamide, ammonium carbamate, ammonium pyrrolidinedithiocarbamate, dimethyl malonate, methyl acetoacetate, N-methyl acetoacetamide, tetramethylammonium thiobenzoate, 2,2,6,6-tetramethyl-3,5-heptanedione, tetramethylthiuram disulfide, lactic acid, ammonium lactate, formic acid, propionic acid, gammabutyrolactone, and mixtures thereof;
and
(G) water,
wherein preferably the pH of the composition is in the range of from 3.5 to 6, preferably in the range of from 4.0 to 5.5.

In the compositions according to the invention as defined above, specifically in the composition according to the second preferred variant of the invention, the one or more solubilizers (A), the one or more etchants comprising fluoride anions (B), the one or more corrosion inhibitors (C) and the one or more chelating agents (D) generally can in each case be used alone (as one single compound) or can be used in combination with other compounds of the same type (solubilizer, etchant, corrosion inhibitor or chelating agent, respectively, as applicable).

A composition according to the invention as defined herein (or a composition according to the invention as described above or below as being preferred, including compositions of the first preferred variant and the second preferred variant) is also preferred wherein the total amount of the one or more solubilizers of component (i.e. the solubilizer component, preferably the preferred solubilizer components as defined above) (A) present is in the range of from 0.01 to 20 wt.-%, preferably in the range of from 2 to 15 wt.-%, more preferably in the range of from 2 to 12 wt.-%; and in some cases preferably in the range of from 2 to 6 wt.-%, based on the total weight of the composition.

A composition according to the invention as defined herein (or a composition according to the invention as described above or below as being preferred, including compositions of the first preferred variant and the second preferred variant) is also preferred wherein the total amount of the one or more etchants of component (B) (comprising fluoride anions, i.e. the etchant component, preferably the preferred etchants of component (B) as defined above) present is in the range of from 0.001 to 1 wt.-%, preferably in the range of from 0.01 to 0.1 wt.-%, more preferably in the range of from 0.02 to 0.08 wt.-%, based on the total weight of the composition. Compositions according to the invention comprising the etchant component (B) in the here defined preferred total amounts have shown a superior balance of acceptable etch rate, in particular for etching a layer comprising or consisting of an aluminium compound, preferably of aluminium oxide, and etch rate selectivity, in particular in the presence of a layer of a low-k material and/or a layer comprising copper and/or cobalt, more in particular a copper layer where a composition according to the first preferred variant of the invention is concerned and more in particular a cobalt layer, where a composition according to the second preferred variant of the invention is concerned.

A composition according to the invention as defined herein (or a composition according to the invention as described above or below as being preferred, including compositions of the first preferred variant and the second preferred variant) is also preferred wherein the total amount of the one or more corrosion inhibitors (i.e. the corrosion inhibitor component, preferably the preferred corrosion inhibitor components as defined above) (C) present is in the range of from 0.01 to 4 wt.-%, preferably in the range of from 0.1 to 2 wt.-%, more preferably in the range of from 0.2 to 1.5 wt.-%, based on the total weight of the composition. Compositions according to the invention comprising the corrosion inhibitor component (C) in the here defined preferred total amounts have shown a superior balance of acceptable etch rate, in particular for etching a layer comprising or consisting of an aluminium compound, preferably of aluminium oxide, and etch rate selectivity, in particular in the presence of a layer of a low-k material and/or a layer comprising copper and/or cobalt layer, more in particular a copper layer where a composition according to the first preferred variant of the invention is concerned and more in particular a cobalt layer (i.e. a selective etch rate in the presence of a cobalt layer), where a composition according to the second preferred variant of the invention is concerned.

A composition according to the invention as defined herein (or a composition according to the invention as described above or below as being preferred, including compositions of the first preferred variant and the second preferred variant) is also preferred wherein the total amount of the one or more chelating agents of component (i.e. the chelating agent component, preferably the preferred chelating agent components as defined above) (D) present is in the range of from 0.01 to 4 wt.-%, preferably in the range of from 0.02 to 1 wt.-%, more preferably in the range of from 0.05 to 0.8 wt.-%, based on the total weight of the composition.

A composition according to the invention as defined herein, preferably a composition according to the first preferred variant (or a composition according to the invention, preferably according to the first preferred variant, as described above or below as being preferred) is also preferred wherein the total amount of the one or more surfactants of component (i.e. the surfactant component, preferably the preferred surfactant components as defined above) (E) present is in the range of from 0.0001 to 1 wt.-%, preferably in the range of from 0.001 to 0.5 wt.-%, more preferably in a total amount in the range of from 0.002 to 0.1 wt.-%, based on the total weight of the composition.

A composition according to the invention as defined herein, preferably a composition of the first preferred variant (or a composition according to the invention, preferably according to the first preferred variant, as described above or below as being preferred) is also preferred wherein the total amount of buffering system of component (i.e. the buffer component) (F) present is in the range of from 0.1 to 10 wt.-%, preferably in the range of from 0.2 to 5 wt.-%, more preferably in the range of from 0.3 to 3 wt.-%, based on the total weight of the composition.

In individual cases, a composition according to the first preferred variant of the invention as defined herein (or a composition according to the first preferred variant of the invention as described above or below as being preferred) is preferred wherein the total amount of the one or more water-miscible organic solvents, (i.e. the solvent component) (H) present is in the range of from 0 to 30 wt.-%, preferably in the range of from 0 to 10 wt.-%, more preferably in the range of from 0 to 7.5 wt.-%, even more preferably in the range of from 0 to 6 wt.-%, based on the total weight of the composition.

A composition according to the invention as defined herein (or a composition according to the invention as described above or below as being preferred, including compositions of the first preferred variant and the second preferred variant) is also preferred wherein the amounts of components (A), (B), (C), (D), (E) (if present), (F) (if present), (G) and (H) (if present) add to a total of 100 wt.-% (i.e. the total weight) of the composition, where preferably water is the balance to a total of 100 wt.-% (i.e. the total weight) of the composition.

A composition according to the first preferred variant of the invention as defined herein is particularly preferred wherein the above-defined total amounts or preferred total amounts of components (A), (B), (C), (D), (E), (F) and (optionally) (H) are combined with the preferred or more preferred components (A), (B), (C), (D), (E), (F) and/or (optionally) (H), as defined above.

A composition according to the first preferred variant of the invention as defined herein (or a composition according to the first preferred variant of the invention as described above or below as being preferred) is particularly preferred wherein the composition consists of (i.e. no further substances are present in addition to component (A) to (H) as defined hereinafter)

(A) one or more solubilizers, selected from the group consisting of 4-methylmorpholine-4-oxide, trimethylamine-N-oxide, triethylamine-N-oxide, triethanolamine-N-oxide; pyridine-N-oxide, N-ethylmorpholine-N-oxide, N-ethylpyrrolidine-N-oxide and mixtures thereof, and preferably the one or more solubilizers is or comprises 4-methylmorpholine-4-oxide,
in a total amount in the range of from 0.01 to 20 wt.-%, preferably in the range of from 2 to 12 wt.-%, more preferably in the range of from 2 to 6 wt.-%, preferably of 4-methylmorpholine-4-oxide, based on the total weight of the composition;

(B) one or more etchants comprising fluoride anions, selected from the group consisting of ammonium fluoride, ammonium bifluoride, triethanolammonium fluoride, diglycolammonium fluoride, methyldiethanolammonium fluoride, tetramethylammonium fluoride, triethylamine trihydrofluoride, hydrogen fluoride, fluoroboric acid, tetrafluoroboric acid, ammonium tetrafluoroborate, fluoroacetic acid, ammonium fluoroacetate, trifluoroacetic acid, fluorosilicic acid, ammonium fluorosilicate, tetrabutylammonium tetrafluoroborate and mixtures thereof, and preferably is or comprises ammonium fluoride,
in a total amount in the range of from 0.01 to 0.1 wt.-%, more preferably in a total amount in the range of from 0.02 to 0.08 wt.-%, preferably of ammonium fluoride, based on the total weight of the composition;

(C) one or more corrosion inhibitors, selected from the group consisting of benzotriazole, 6-methyl-benzotriazole, 5-methyl-benzotriazole, ethylene urea, ethylene thiourea, 1,2,4-triazole, 5-aminotetrazole, 1-hydroxybenzotriazole, 5-amino-1,3,4-thiadiazol-2-thiol, 3-amino-1H-1,2,4 triazole, 3,5-diamino-1,2,4-triazole, tolyltriazole, 5-phenylbenzotriazole, 5-nitro-benzotriazole, 3-amino-5-mercapto-1,2,4-triazole, 1-amino-1,2,4-triazole, 2-(5-amino-pentyl)-benzotriazole, 1-amino-1,2,3-triazole, 1-amino-5-methyl-1,2,3-triazole, 3-mercapto-1,2,4-triazole, 3-isopropyl-1,2,4-triazole, 5-phenylthiol-benzotriazole, halobenzotriazoles (where halo is selected from the group consisting of F, Cl, Br and I), naphthotriazole, 1H-tetrazole-5-acetic acid, 2-mercaptobenzothiazole, 1-phenyl-2-tetrazoline-5-thione, 2-mercaptobenzimidazole, 4-methyl-2-phenylimidazole, 2-mercaptothiazoline, 2,4-diamino-6-methyl-1,3,5-triazine, thiazole, imidazole, benzimidazole, triazine, methyltetrazole, 1,3-dimethyl-2-imidazolidinone, 1,5-pentamethylenetetrazole, 1-phenyl-5-mercaptotetrazole, 2H-imidazole-2-thione, 4-methyl-4H-1,2,4-triazole-3-thiol, 5-amino-1,3,4-thiadiazole-2-thiol, benzothiazole, tritolyl phosphate, indazole, adenine, cytosine, guanine, thymine, 2,2'-azanediyldiacetic acid, propanethiol, citric acid, ascorbic acid, thiourea, 1,1,3,3-tetramethylurea, urea, uric acid, glycine, dodecylphosphonic acid, oxalic acid, malonic acid, succinic acid, nitrilotriacetic acid and mixtures thereof, and preferably is selected from the group consisting of benzotriazole, 6-methyl-benzotriazole and mixtures thereof,
in a total amount in the range of from 0.01 to 4 wt.-%, preferably in a total amount in the range of from 0.1 to 2 wt.-%, more preferably in a total amount in the range of from 0.2 to 1.5 wt.-%, preferably selected from the group consisting of benzotriazole, 6-methyl-benzotriazole and mixtures thereof, based on the total weight of the composition;

(D) one or more chelating agents selected from the group consisting of 1,2-cyclohexylenedinitrilotetraacetic acid, 1,1,1,5,5,5-hexafluoro-2,4-pentanedione, acetylacetonate, 2,2'-azanediyldiacetic acid, ethylenediaminetetraacetic acid, etidronic acid, methanesulfonic acid, acetylacetone, 1,1,1-trifluoro-2,4-pentanedione, 1,4-benzoquinone, 8-hydroxyquinoline, salicylidene aniline; tetrachloro-1,4-benzoquinone, 2-(2-hydroxyphenyl)-benzoxazol, 2-(2-hydroxyphenyl)-benzothiazole, hydroxyquinoline sulfonic acid, sulfosalicylic acid, salicylic acid, pyridine, 2-ethylpyridine, 2-methoxypyridine, 3-methoxypyridine, 2-picoline, dimethylpyridine, piperidine, piperazine, triethylamine, triethanolamine, ethylamine, methylamine, isobutylamine, tert-butylamine, tributylamine, dipropylamine, dimethylamine, diglycol amine, monoethanolamine, methyldiethanolamine, pyrrole, isoxazole, bipyridine, pyrimidine, pyrazine, pyridazine, quinoline, isoquinoline, indole, 1-methylimidazole, diisopropylamine, diisobutylamine, aniline, pentamethyldiethylenetriamine, acetoacetamide, ammonium carbamate, ammonium pyrrolidinedithiocarbamate, dimethyl malonate, methyl acetoacetate, N-methyl acetoacetamide, tetramethylammonium thiobenzoate, 2,2,6,6-tetramethyl-3,5-heptanedione, tetramethylthiuram disulfide, lactic acid, ammonium lactate, formic acid, propionic acid, gamma-butyrolactone, and mixtures thereof, and preferably is or comprises 1,2-cyclohexylenedinitrilotetraacetic acid,
in a total amount in the range of from 0.01 to 4 wt.-%, preferably in a total amount in the range of from 0.02 to 1 wt.-%, more preferably in a total amount in the range of from 0.05 to 0.8 wt.-%, preferably of 1,2-cyclohexylenedinitrilotetraacetic acid, based on the total weight of the composition;

(E) one or more surfactants selected from the group consisting of (i) anionic surfactants, preferably selected from the group consisting of ammonium lauryl sulfate, fluorosurfactants, preferably selected from the group consisting of perfluorinated alkylsulfonamide salts (preferably perfluorinated, N-substituted alkylsulfonamide ammonium salts), perfluorooctanesulfonate, perfluorobutanesulfonate, perfluorononanoate and perfluorooctanoate; alkyl-aryl ether phosphates and alkyl ether phosphates, (ii) zwitterionic surfactants, preferably selected from the group consisting of (3-[(3-cholamidopropyl)dimethylammonio]-1-propane-sulfonate), cocamidopropyl hydroxysultaine, {[3-(dodecanoylamino)propyl](dimethy)ammonio}acetate, phosphatidylserine, phosphatidylethanolamine, phosphatidylcholine, (iii) non-ionic surfactants, preferably selected from the group consisting of glucoside alkyl ethers, glycerol alkyl ethers, cocamide ethanolamines and lauryldimethylaminoxide; and preferably the one or more surfactants are or comprise perfluorinated, N-substituted alkylsulfonamide ammonium salts,
    in a total amount in the range of from 0.0001 to 1 wt.-%, preferably in a total amount in the range of from 0.001 to 0.5 wt.-%, more preferably in a total amount in the range of from 0.002 to 0.1 wt.-%, preferably selected from the group consisting of perfluorinated, N-substituted alkylsulfonamide ammonium salts, based on the total weight of the composition;
(F) a buffering system which is suitable to buffer the pH of the composition in the range of from 6.4 to 7.5, preferably in the range of from 6.8 to 7.5, more preferably in the range of from 7.0 to 7.4, preferably selected from the group consisting of a phosphate buffer comprising $NaH_2PO_4$ and $Na_2HPO_4$, a HEPES buffer comprising 2-[4-(2-hydroxyethyl)piperazin-1-yl]ethanesulfonic acid, a TRIS buffer comprising tris(hydroxymethyl)-aminomethane and an ammonium acetate buffer, and more preferably is or comprises an ammonium acetate buffer,
    in a total amount in the range of from 0.1 to 10 wt.-%, preferably in a total amount in the range of from 0.2 to 5 wt.-%, more preferably in a total amount in the range of from 0.3 to 3 wt.-%, based on the total weight of the composition;
(G) water as balance to a total of 100 wt.-% of the composition in each case,
and
(H) one or more water-miscible organic solvents, preferably selected from the group consisting of tetrahydrofuran (THF), N-methylpyrrolidone (NMP), dimethyl formamide (DMF), dimethyl sulfoxide (DMSO) and sulfolane (2,3,4,5-tetrahydrothiophene-1,1-dioxide) and mixtures thereof,
    in a total amount in the range of from 0 to 30 wt.-%, preferably in the range of from 0 to 10 wt.-%, more preferably in a total amount in the range of from 0 to 7.5 wt.-%, even more preferably in a total amount in the range of from 0 to 6 wt.-%, based on the total weight of the composition,
wherein the pH of the composition is in the range of from 6.4 to 7.5, preferably in the range of from 6.8 to 7.5, more preferably in the range of from 7.0 to 7.4,
and
wherein the wt.-% total amounts of components (A), (B), (C), (D), (E), (F), (G) and (if present) (H) add to 100 wt.-% in each case.

In the above-defined particularly preferred composition of the first preferred variant of the invention, the preferred or more preferred components (A), (B), (C), (D), (E), (F) and/or (optionally) (H) and/or the above-defined amounts or preferred amounts of components (A), (B), (C), (D), (E), (F) and (optionally) (H) can be combined to result in an even more preferred composition according to the first preferred variant of the invention.

A composition according to the first preferred variant of the invention as defined herein (or a composition according to the first preferred variant of the invention as described above as being preferred) is specifically preferred wherein the composition consists of
(A) 4-methylmorpholine-4-oxide as solubilizer,
    preferably in a total amount in the range of from 0.01 to 20 wt.-%, more preferably in the range of from 2 to 12 wt.-%, even more preferably in the range of from 2 to 6 wt.-%, based on the total weight of the composition;
(B) ammonium fluoride as etchant,
    preferably in a total amount in the range of from 0.01 to 0.1 wt.-%, more preferably in a total amount in the range of from 0.02 to 0.08 wt.-%, based on the total weight of the composition;
(C) one or more corrosion inhibitors, selected from the group consisting of benzotriazole, 6-methyl-benzotriazole and mixtures thereof,
    preferably in a total amount in the range of from 0.01 to 4 wt.-%, more preferably in a total amount in the range of from 0.1 to 2 wt.-%, even more preferably in a total amount in the range of from 0.2 to 1.5 wt.-%, based on the total weight of the composition;
(D) 1,2-cyclohexylenedinitrilotetraacetic acid as chelating agent,
    preferably in a total amount in the range of from 0.01 to 4 wt.-%, more preferably in a total amount in the range of from 0.02 to 1 wt.-%, even more preferably in a total amount in the range of from 0.05 to 0.8 wt.-%, based on the total weight of the composition;
(E) one or more surfactants wherein the or at least one of the one or more surfactants is a perfluorinated, N-substituted alkylsulfonamide ammonium salt,
    preferably in a total amount in the range of from 0.0001 to 1 wt.-%, more preferably in a total amount in the range of from 0.001 to 0.5 wt.-%, even more preferably in a total amount in the range of from 0.002 to 0.1 wt.-%, based on the total weight of the composition;
(F) a buffering system which is suitable to buffer the pH of the composition in the range of from 6.4 to 7.5, preferably in the range of from 6.8 to 7.5, more preferably in the range of from 7.0 to 7.4, and which is preferably an ammonium acetate buffer,
    preferably in a total amount in the range of from 0.1 to 10 wt.-%, more preferably in a total amount in the range of from 0.2 to 5 wt.-%, even more preferably in a total amount in the range of from 0.3 to 3 wt.-%, based on the total weight of the composition
and
(G) water as balance to a total of 100 wt.-% of the composition in each case,
wherein the pH of the composition is in the range of from 6.4 to 7.5, preferably in the range of from 6.8 to 7.5, more preferably in the range of from 7.0 to 7.4,
and
wherein preferably the wt.-% total amounts of components (A), (B), (C), (D), (E), (F) and (G) add to 100 wt.-% in each case.

A composition according to the second preferred variant of the invention as defined herein (or a composition according to the second preferred variant of the invention as described above or below as being preferred) is preferred wherein:
(A) the or at least one component (A) is a compound of formula I as defined above (or a preferred compound of formula I as defined above) and preferably the or at least one component (A) is N-formylmorpholine,
and preferably component (A) is present in a total amount in the range of from 0.01 to 20 wt.-%, more preferably in the range of from 2 to 15 wt.-%, even more preferably in the range of from 2 to 12 wt.-% and yet even more preferably in the range of from 5 to 12 wt.-%, based on the total weight of the composition.

A composition according to the second preferred variant of the invention as defined herein (or a composition according to the second preferred variant of the invention as described above or below as being preferred) is also preferred wherein:
(B) component (B) is selected from the group consisting of ammonium fluoride, ammonium bifluoride, triethanolammonium fluoride, diglycolammonium fluoride, methyldiethanolammonium fluoride, tetramethylammonium fluoride, triethylamine trihydrofluoride, hydrogen fluoride, fluoroboric acid, tetrafluoroboric acid, ammonium tetrafluoroborate, fluoroacetic acid, ammonium fluoroacetate, trifluoroacetic acid, fluorosilicic acid, ammonium fluorosilicate, tetrabutylammonium tetrafluoroborate and mixtures thereof;
wherein preferably the or at least one component (B) is ammonium fluoride and more preferably component (B) is ammonium fluoride,
and preferably component (B) is present in a total amount in the range of from 0.01 to 0.1 wt.-%, more preferably in a total amount in the range of from 0.02 to 0.08 wt.-%, based on the total weight of the composition.

A composition according to the second preferred variant of the invention as defined herein (or a composition according to the second preferred variant of the invention as described above or below as being preferred) is also preferred wherein:
(C) the or at least one component (C) is selected from the group consisting of
benzotriazole which is unsubstituted or substituted once or twice, preferably once, independently by $C_{1-4}$-alkyl and/or (preferably "or") by halogen;
succinic acid
and
mixtures thereof;
and preferably component (C) is present in a total amount in the range of from 0.01 to 4 wt.-%, more preferably in a total amount in the range of from 0.1 to 2 wt.-% and yet more preferably in a total amount in the range of from 0.2 to 1.5 wt.-%, based on the total weight of the composition.

A composition according to the second preferred variant of the invention as defined herein (or a composition according to the second preferred variant of the invention as described above or below as being preferred) is likewise preferred wherein:
(D) the or at least one component (D) is histidine, preferably L-histidine;
and preferably component (D) is present in a total amount in the range of from 0.01 to 4 wt.-%, more preferably in a total amount in the range of from 0.02 to 1 wt.-% and yet more preferably in a total amount in the range of from 0.05 to 0.8 wt.-%, based on the total weight of the composition.

A composition according to the second preferred variant of the invention as defined herein (or a composition according to the second preferred variant of the invention as described above or below as being preferred) is particularly preferred wherein:
(A) the or at least one component (A) is a compound of formula I as defined above (or a preferred compound of formula I as defined above) and preferably the or at least one component (A) is N-formylmorpholine,
and preferably is present in a total amount in the range of from 0.01 to 20 wt.-%, more preferably in the range of from 2 to 15 wt.-%, even more preferably in the range of from 2 to 12 wt.-% and yet even more preferably in the range of from 5 to 12 wt.-%, based on the total weight of the composition;
(B) component (B) is selected from the group consisting of ammonium fluoride, ammonium bifluoride, triethanolammonium fluoride, diglycolammonium fluoride, methyldiethanolammonium fluoride, tetramethylammonium fluoride, triethylamine trihydrofluoride, hydrogen fluoride, fluoroboric acid, tetrafluoroboric acid, ammonium tetrafluoroborate, fluoroacetic acid, ammonium fluoroacetate, trifluoroacetic acid, fluorosilicic acid, ammonium fluorosilicate, tetrabutylammonium tetrafluoroborate and mixtures thereof;
wherein preferably the or at least one component (B) is ammonium fluoride and more preferably component (B) is ammonium fluoride,
and preferably is present in a total amount in the range of from 0.01 to 0.1 wt.-%, more preferably in a total amount in the range of from 0.02 to 0.08 wt.-%, based on the total weight of the composition;
(C) the or at least one component (C) is selected from the group consisting of
benzotriazole which is unsubstituted or substituted once or twice, preferably once, independently by $C_{1-4}$-alkyl and/or (preferably "or") by halogen;
succinic acid
and
mixtures thereof;
and preferably is present in a total amount in the range of from 0.01 to 4 wt.-%, more preferably in a total amount in the range of from 0.1 to 2 wt.-% and yet more preferably in a total amount in the range of from 0.2 to 1.5 wt.-%, based on the total weight of the composition;
(D) the or at least one component (D) is histidine, preferably L-histidine;
and preferably is present in a total amount in the range of from 0.01 to 4 wt.-%, more preferably in a total amount in the range of from 0.02 to 1 wt.-% and yet more preferably in a total amount in the range of from 0.05 to 0.8 wt.-%, based on the total weight of the composition;
and
(G) component (G) is water, and preferably is present as balance to a total of 100 wt.-% of the composition in each case,
wherein the pH of the composition is in the range of from 3.5 to 6, preferably in the range of from 4.0 to 5.5
and
wherein preferably the wt.-% total amounts of components (A), (B), (C), (D) and (G) add to 100 wt.-% in each case.

A composition according to the second preferred variant of the invention as defined herein (or a composition according to the second preferred variant of the invention as described above or below as being preferred) is also preferred wherein:

(A) component (A) is a compound of formula I as defined above (or a preferred compound of formula I as defined above), wherein preferably component (A) is N-formylmorpholine,
and is present in a total amount in the range of from 0.01 to 20 wt.-%, preferably in the range of from 2 to 15 wt.-%, more preferably in the range of from 2 to 12 wt.-% and even more preferably in the range of from 5 to 12 wt.-%, based on the total weight of the composition;

(B) component (B) is selected from the group consisting of ammonium fluoride, ammonium bifluoride, triethanolammonium fluoride, diglycolammonium fluoride, methyldiethanolammonium fluoride, tetramethylammonium fluoride, triethylamine trihydrofluoride, hydrogen fluoride, fluoroboric acid, tetrafluoroboric acid, ammonium tetrafluoroborate, fluoroacetic acid, ammonium fluoroacetate, trifluoroacetic acid, fluorosilicic acid, ammonium fluorosilicate, tetrabutylammonium tetrafluoroborate and mixtures thereof;
wherein preferably the or at least one component (B) is ammonium fluoride and more preferably component (B) is ammonium fluoride,
and is present in a total amount in the range of from 0.01 to 0.1 wt.-%, preferably in a total amount in the range of from 0.02 to 0.08 wt.-%, based on the total weight of the composition;

(C) component (C) is selected from the group consisting of
benzotriazole which is unsubstituted or substituted once or twice, preferably once, independently by $C_{1-4}$-alkyl and/or (preferably "or") by halogen;
succinic acid
and
mixtures thereof;
and is present in a total amount in the range of from 0.01 to 4 wt.-%, preferably in a total amount in the range of from 0.1 to 2 wt.-%, more preferably in a total amount in the range of from 0.2 to 1.5 wt.-%, based on the total weight of the composition (D) component (D) is histidine, preferably L-histidine;
and is present in a total amount in the range of from 0.01 to 4 wt.-%, preferably in a total amount in the range of from 0.02 to 1 wt.-%, more preferably in a total amount in the range of from 0.05 to 0.8 wt.-%, based on the total weight of the composition;
and
(G) component (G) is water and is present as balance to a total of 100 wt.-% of the composition in each case,
wherein the pH of the composition is in the range of from 3.5 to 6, preferably in the range of from 4.0 to 5.5
and
wherein the wt.-% total amounts of components (A), (B), (C), (D) and (G) add to 100 wt.-% in each case.

It has been found in own experiments that a composition according to the second preferred variant which comprises histidine, preferably L-histidine, as the or at least one component (D), in particular as the component (D), shows a more selective etch rate in the presence of a cobalt layer than a composition according to the second preferred variant which does not comprise histidine as the or at least one component (D), in particular as the component (D).

A composition according to the second preferred variant of the invention as defined herein (or a composition according to the second preferred variant of the invention as described above or below as being preferred) is also preferred wherein the or at least one component (A) is N-formylmorpholine (CAS RN 4394-85-8) and wherein preferably component (A) is N-formylmorpholine.

Compositions according to the second preferred variant of the invention comprising N-formylmorpholine as solubilizer component (A), in particular in the preferred total amounts as specified above, have shown excellent stability of the composition against precipitation, and enhanced solubility, even at temperatures below room temperature.

Compositions according to the second preferred variant of the invention wherein component (C) is selected from the group consisting of
benzotriazole which is unsubstituted or substituted once or twice, preferably once, independently by $C_{1-4}$-alkyl and/or (preferably "or") halogen; preferably 5-methyl-2H-benzotriazole and 5-chloro-2H-benzotriazole;
succinic acid
and
mixtures thereof,
have shown a stable and reproducible selective etch rate for etching a layer comprising or consisting of an aluminium compound, in particular of aluminium oxide, in the presence of a layer of a low-k material and/or a layer comprising copper and/or cobalt, in particular in the presence of a layer of a low-k material and/or a cobalt layer (i.e. a selective etch rate in the presence of a cobalt layer).

Particularly preferred is a composition according to the second preferred variant of the invention as defined herein (or a composition according to the second preferred variant of the invention as described above or below as being preferred), comprising or consisting of (A) N-formylmorpholine as solubilizer,
preferably in a total amount in the range of from 0.01 to 20 wt.-%, more preferably in the range of from 2 to 15 wt.-%, even more preferably in the range of from 2 to 12 wt.-% and yet even more preferably in the range of from 5 to 12 wt.-%, based on the total weight of the composition;

(B) ammonium fluoride as etchant;
preferably in a total amount in the range of from 0.01 to 0.1 wt.-%, more preferably in a total amount in the range of from 0.02 to 0.08 wt.-%, based on the total weight of the composition;

(C) a corrosion inhibitor selected from the group consisting of
5-methyl-2H-benzotriazole,
5-chloro-2H-benzotriazole,
succinic acid
and
mixtures thereof;
preferably in a total amount in the range of from 0.01 to 4 wt.-%, more preferably in a total amount in the range of from 0.1 to 2 wt.-%, yet more preferably in a total amount in the range of from 0.2 to 1.5 wt.-%, based on the total weight of the composition (D) histidine, preferably L-histidine, as chelating agent;
preferably in a total amount in the range of from 0.01 to 4 wt.-%, more preferably in a total amount in the range of from 0.02 to 1 wt.-%, yet more preferably in a total amount in the range of from 0.05 to 0.8 wt.-%, based on the total weight of the composition;
and
(G) water, preferably as balance to a total of 100 wt.-% of the composition in each case, wherein the pH of the composition is in the range of from 3.5 to 6, preferably in the range of from 4.0 to 5.5
and
wherein preferably the wt.-% total amounts of components (A), (B), (C), (D) and (G) add to 100 wt.-% in each case.

The present invention also relates to the use of a composition according to the invention (including a use of the composition of the first preferred variant and of the composition of the second preferred variant) as defined herein (or a respective use according to the invention as described herein as being preferred), for selectively etching a layer comprising an aluminium compound, preferably of aluminium oxide, in the presence of a layer of a low-k material and/or a layer comprising copper and/or cobalt;

preferably in the presence of a layer of a low-k material and/or a layer comprising copper, preferably a copper layer, where a composition of the first preferred variant of the present invention is used;

and/or preferably in the presence of a layer of a low-k material and/or a layer comprising cobalt, preferably a cobalt layer, where a composition of the second preferred variant of the present invention is used;

and/or for selectively removing from a substrate a layer comprising an aluminium compound, preferably aluminium oxide, in the presence of a layer of a low-k material and/or a layer comprising copper and/or cobalt;

preferably in the presence of a layer of a low-k material and/or a layer comprising copper, preferably a copper layer, where a composition of the first preferred variant of the present invention is used;

and/or preferably in the presence of a layer of a low-k material and/or a layer comprising cobalt, preferably a cobalt layer, where a composition of the second preferred variant of the present invention is used;

and/or for selectively removing from the surface of a semiconductor substrate a layer comprising an aluminium compound, preferably aluminium oxide, in the presence of a layer of a low-k material and/or a layer comprising copper and/or cobalt;

preferably in the presence of a layer of a low-k material and/or a layer comprising copper where a composition of the first preferred variant of the present invention is used;

and/or preferably in the presence of a layer of a low-k material and/or a layer comprising cobalt, preferably a cobalt layer, where a composition of the second preferred variant of the present invention is used.

Generally, all aspects of the present invention discussed herein in the context of the inventive composition (including the first preferred variant and the second preferred variant) apply mutatis mutandis to the use of said composition according to the present invention (including the use of the first preferred variant and the use of the second preferred variant), as defined here above and below. And likewise all aspects of the use of said composition according to the present invention discussed herein apply mutatis mutandis to the inventive composition.

A use according to the invention (including a use of the composition of the first preferred variant and of the composition of the second preferred variant) as defined above (or a respective use according to the invention as described herein as being preferred) is particularly preferred wherein the use is in a two-step-process of removing (i) a metal hard mask, preferably selected from the group consisting of a Ti hard mask, a TiN hard mask, a Ta hard mask, a TaN hard mask, an Al hard mask, a $HfO_x$ (i.e. Hafnium oxide) hard mask and an AlCu (i.e. an AlCu alloy) hard mask, more preferably a TiN hard mask and (ii) an etch-stop layer of an aluminium compound deposited on a layer comprising copper, preferably a copper layer, and/or a layer comprising cobalt, preferably a cobalt layer, wherein preferably the use is in the second step (ii);

and wherein preferably the use of a composition of the first preferred variant of the present invention is in said two-step process wherein the etch-stop layer of an aluminium compound is deposited on a layer comprising copper, preferably a copper layer;

and/or wherein preferably the use of a composition of the second preferred variant of the present invention is in said two-step process wherein the etch-stop layer of an aluminium compound is deposited on a layer comprising cobalt, preferably a cobalt layer.

In the preferred use in the two-step process according to the invention as defined here above, preferably the process step (i) of removing a metal hard mask is the first process step and the process step (ii) of removing an etch-stop layer is the second process step. Said second process step can be performed directly after said first process step or there can be performed one or more other process steps between performing said first process step and said second process step.

A use according to the invention (including a use of the composition of the first preferred variant and of the composition of the second preferred variant) as defined above (or a respective use according to the invention as described herein as being preferred) is also preferred wherein the etch-stop layer of an aluminium compound, preferably of aluminium oxide, before etching has a maximum thickness of 30 nm or below, preferably of 20 nm or below, more preferably of 10 nm or below and even more preferably of 5 nm or below.

A use according to the invention as defined above (or a use according to the invention as described herein as being preferred) is also preferred wherein the two-step process is part of a damascene process for manufacturing integrated circuit interconnects.

The present invention also relates to a process for the manufacture of a semiconductor device, comprising the step of selectively etching at least one layer comprising or consisting of an aluminium compound, preferably of aluminium oxide, in the presence of a layer of a low-k material and/or a layer comprising copper and/or cobalt, by contacting the at least one layer of an aluminium compound at least once with a composition (including a composition of the first preferred variant and a composition of the second preferred variant) according to the invention as defined herein (or a composition according to the invention as described herein as being preferred).

Where the process comprises the step of selectively etching at least one layer comprising or consisting of an aluminium compound, preferably of aluminium oxide, in the presence of a layer of a low-k material and/or a layer comprising copper, preferably a copper layer, contacting the at least one layer of an aluminium compound at least once with a composition according to the first preferred variant of the invention as defined herein (or a composition according to the first preferred variant of the invention as described herein as being preferred) is preferred.

Where the process comprises the step of selectively etching at least one layer comprising or consisting of an aluminium compound, preferably of aluminium oxide, in the presence of a layer of a low-k material and/or a layer comprising cobalt, preferably a cobalt layer, contacting the at least one layer of an aluminium compound at least once with a composition according to the second preferred variant of the invention as defined herein (or a composition according to the second preferred variant of the invention as described herein as being preferred) is preferred.

Generally, all aspects of the present invention discussed herein in the context of the inventive composition and/or the inventive use of said composition apply mutatis mutandis to the process for the manufacture of a semiconductor device of the present invention, as defined here above and below. And likewise all aspects of the process for the manufacture of a semiconductor device of the present invention apply mutatis mutandis to the inventive composition and/or the inventive use of said composition.

A process according to the invention as defined above is preferred wherein said etching is conducted in the presence of a layer of a low-k material and a layer comprising copper and/or cobalt, preferably in the presence of a layer of a low-k material and a layer comprising copper, preferably a copper layer, where a composition according to the first preferred variant of the invention as defined herein (or a composition according to the first preferred variant of the invention as described herein as being preferred) is used and preferably in the presence of a layer of a low-k material and a layer comprising cobalt, preferably a cobalt layer, where a composition according to the second preferred variant of the invention as defined herein (or a composition according to the second preferred variant of the invention as described herein as being preferred) is used.

A process according to the invention as defined above (or a process according to the invention as described herein as being preferred) is also preferred wherein said at least one layer comprising or consisting of an aluminium compound is a top layer and the layer comprising copper and/or cobalt, is a lower layer covered by the top layer, with or without at least one further layer being present in between the top layer and the lower layer, preferably without at least one (i.e. without any) further layer being present in between the top layer and the lower layer.

A process according to the invention as defined above (or a process according to the invention as described herein as being preferred) is also preferred wherein the process for manufacturing a semiconductor device is a damascene process for manufacturing integrated circuit interconnects.

A process according to the invention as defined above (or a process according to the invention as described herein as being preferred) is also preferred wherein the process comprises a two-step cleaning process, preferably a cleaning process for a semiconductor device, comprising the steps of
  removing in a first step a metal hard mask, preferably selected from the group consisting of a Ti hard mask, a TiN hard mask, a Ta hard mask, a TaN hard mask, an Al hard mask, a HfO$_x$ (i.e. Hafniumoxide) hard mask and an AlCu hard mask; more preferably a TiN hard mask,
  before selectively etching in a separate second step the at least one layer comprising or consisting of an aluminium compound, preferably of aluminium oxide.

Preferably the metal hard mask in the preferred process of the invention as defined here above is selected from the group consisting of a Ti hard mask, a TiN hard mask, a Ta hard mask, a TaN hard mask, an Al hard mask, a HfO$_x$ (i.e. Hafniumoxide) hard mask and an AlCu (i.e. an AlCu alloy) hard mask. More preferably the metal hard mask is a TiN hard mask.

In the preferred two-step process according to the invention as defined here above, said separate second process step can be performed directly after said first process step or there can be performed one or more other process steps between performing said first process step and said separate second process step.

A process according to the invention as defined above (or a process according to the invention as described herein as being preferred) is also preferred wherein the at least one layer comprising or consisting of an aluminium compound, preferably of aluminium oxide, before etching has a maximum thickness of 30 nm or below, preferably of 20 nm or below, more preferably of 10 nm or below and even more preferably of 5 nm or below. In some cases a process according to the invention as defined above (or a process according to the invention as described herein as being preferred) is preferred wherein the at least one layer comprising or consisting of an aluminium compound, preferably of aluminium oxide, has a maximum thickness of 2 nm or below, preferably of 1 nm or below, more preferably of 0.5 nm or below.

EXAMPLES

The following examples are meant to further explain the invention without limiting its scope.

Example 1: Preparation of Compositions According to the Invention (First Preferred Variant) and of Comparative Compositions (not According to the Invention)

The following preferred compositions according to the first preferred variant of the invention (marked as "I", i.e. compositions I1 to I8) were prepared by mixing the components (A) to (G) or (A) to (H), as applicable. Details are given below in table 1a. Further compositions according to the invention (marked as "I", i.e. compositions I9 to I13) were prepared by mixing the components (A) to (G) or (A) to (H), as applicable. Details are given below in table 1b. In addition, comparative compositions (not according to the invention, marked as "C", i.e. compositions C1 to C2) were also prepared in a similar manner, as shown in more detail in table 1c below. For adjusting the pH of the different compositions, a total amount of an acidic buffer component (acetic acid as a 96% w/w solution in water where an acetate buffer was used) was added to the composition, followed by a suitable amount of the corresponding basic (alkaline) buffer component (ammonia as a 29 wt.-% solution in water where an acetate buffer was used) until the desired pH of the composition was reached.

TABLE 1a

Preferred test compositions according to the invention (first preferred variant)

| Component | Constituent | Composition [wt.-%] | | | | | | | |
|---|---|---|---|---|---|---|---|---|---|
| | | I1 | I2 | I3 | I4 | I5 | I6 | I7 | I8 |
| (A) | 4-MM-4-O | 5.0 | 5.0 | 2.5 | 5.0 | 5.0 | 5.0 | 5.0 | 5.0 |
| (B) | NH$_4$F | 0.06 | 0.03 | 0.06 | 0.06 | 0.06 | 0.06 | 0.06 | 0.06 |
| (C) | 6-Me-BTA | 0.5 | 0.5 | 0.5 | 0.5 | 0.5 | 0.5 | 0.5 | 0.25 |
| (C) | BTA | 0.5 | 0.5 | 0.5 | 0.5 | 0.5 | 0.5 | 0.5 | 0.25 |
| (D) | CDTA | 0.1 | 0.1 | 0.1 | 0.1 | 0.1 | 0.1 | 0.1 | 0.1 |
| (E) | PNAAS | 0.02 | 0.02 | 0.02 | 0.02 | 0.02 | 0.02 | 0.02 | 0.004 |
| (F) | Acetic acid | 0.5 | 0.5 | 0.3 | 0.3 | 0.7 | 0.6 | 0.6 | 0.6 |
| (F) | Ammonia | 0.2 | 0.2 | 0.2 | 0.2 | 0.3 | 0.2 | 0.2 | 0.2 |
| (G) | Water | 93.12 | 93.15 | 90.92 | 88.32 | 87.82 | 88.02 | 93.02 | 93.536 |
| (H) | Sulfolane | 0 | 0 | 5.0 | 5.0 | 5.0 | 5.0 | 0 | 0 |
| — | pH: | 7.4 | 7.4 | 7.3 | 7.3 | 7.1 | 6.4 | 6.4 | 7.0 |

TABLE 1b

Further test compositions according to the invention (first preferred variant)

| Component | Constituent | Composition [wt.-%] | | | | |
|---|---|---|---|---|---|---|
| | | I9 | I10 | I11 | I12 | I13 |
| (A) | 4-MM-4-O | 5.0 | 5.0 | 7.5 | 7.5 | 7.5 |
| (B) | NH$_4$F | 0.06 | 0.06 | 0.06 | 0.06 | 0.06 |
| (C) | 6-Me-BTA | 0.5 | 0.5 | 0.5 | 0.5 | 0.6 |
| (C) | BTA | 0.5 | 0.5 | 0.5 | 0.5 | 0.6 |
| (D) | CDTA | 0.1 | 0.1 | 0.1 | 0.1 | 0.1 |
| (E) | PNAAS | 0.02 | 0.02 | 0.02 | 0 | 0 |
| (F) | Acetic acid | 0.75 | 0.75 | 0.5 | 0.5 | 0.5 |
| (F) | Ammonia | 0.3 | 0.3 | 0.2 | 0.2 | 0.22 |
| (G) | Water | 87.77 | 92.77 | 83.12 | 83.14 | 82.92 |
| (H) | Sulfalane | 5.0 | 0 | 0 | 0 | 0 |
| — | BDG | 0 | 0 | 7.5 | 7.5 | 7.5 |
| — | pH: | 6.3 | 6.3 | 7.4 | 7.4 | 7.4 |

TABLE 1c

Comparative test compositions

| Component | Constituent | Composition [wt.-%] | |
|---|---|---|---|
| | | C1 | C2 |
| (A) | 4-MM-4-O | 7.5 | 7.5 |
| (B) | NH$_4$F | 0.06 | 0.06 |
| (C) | 6-Me-BTA | 0 | 0 |
| (C) | BTA | 0 | 0 |
| (D) | CDTA | 0.1 | 0.1 |
| (E) | PNAAS | 0.02 | 0 |
| (F) | Acetic acid | 0.5 | 0.5 |
| (F) | Ammonia* | 0.2 | 0.22 |
| (G) | Water | 84.1 | 84.12 |
| (H) | Sulfolane | 0 | 0 |
| — | BDG | 7.5 | 7.5 |
| — | pH: | 8.2 | 8.2 |

BDG: butyl diglycol (diethyleneglycol butyl ether)
All wt.-% of constituents in tables 1a, 1b and 1c are calculated as pure, undiluted compounds.

Example 2: Determination of Aluminum Oxide (AlOx) and Corner Etch Results of Test Compositions (First Preferred Variant)

Si wafers or wafer pieces (collectively referred to as "test wafers" in the following) with the appropriate types of outer layers were obtained from commercial sources. The test wafers were pre-treated as applicable: Cu was immersed into an oxalic acid solution for 20-30 s and then rinsed with water and dried. AlOx-coated surfaces were not pre-treated. The copper and AlO$_x$-layers on the test wafers had a thickness of 100 Å in each case.

Aluminum oxide (AlO$_x$)-coated surfaces were used as a representative model for layers of (comprising or consisting of) an aluminium compound (as defined above).

The test compositions (as defined in tables 1a, 1b and 1c) were prepared and the test wafers (see above) were contacted with the test compositions in a glass beaker, at a temperature of 60° C. and for a reaction time period of 1 min in the case of AlO$_x$ surfaces and for a reaction time period of from 5 min to 10 min in the case of Cu surfaces, and then withdrawn from the test compositions, rinsed with water or isopropanol and dried with nitrogen gas.

The thicknesses of the copper and aluminium oxide layers on the test wafers were determined before and after contact with the test compositions by X-ray fluorescence analysis. Experiments were repeated at least three times to ensure reproducibility.

The difference of the measured value of the thickness of a copper or an AlO$_x$ layer, respectively, before its contact with a test composition, minus the measured value of the thickness of the same copper or aluminium oxide layer, respectively, after its contact with the test composition was determined in each case as the total etch loss and the total etch loss so determined was divided by the process time to yield the etch rate. The results are shown in table 2 below as etch rate of a layer after contact with a test composition in Å/min (each given value in table 2 representing the average of at least three experiments).

TABLE 2

Aluminium oxide and copper etch results of the test compositions (first preferred variant)

| Composition | Etch rates per layer [Å/min] | |
|---|---|---|
| | Cu | AlO$_x$ |
| I1 | 0.1 | 96 |
| I2 | 0 | 50 |
| I3 | 0.1 | 55 |
| I4 | 0.1 | 53 |
| I5 | 0.1 | 79.1 |
| I6 | 0.1 | 88 |
| I7 | 0.1 | >100 |
| I9 | 0.1 | >100 |
| I10 | 0.1 | >100 |
| I11 | 5 | >100 |
| I12 | 7.4 | >100 |

TABLE 2-continued

Aluminium oxide and copper etch results of the test compositions (first preferred variant)

| | Etch rates per layer [Å/min] | |
|---|---|---|
| Composition | Cu | AlO$_x$ |
| I13 | 6 | >100 |
| C1 | >50 | 25 |
| C2 | >50 | 22 |

Etch rate values of ">100" in table 2 for AlO$_x$—layers on a Si wafer have the meaning that the entire AlO$_x$-layer was removed within the applicable reaction time period of one minute or before said applicable reaction time period of one minute had passed, with the effect that an exact etch rate could not be measured in these cases (such cases also being referred to as cases of "over-etching" hereinafter).

From the test results received, the following observations can be made:

The preferred test compositions according to the first preferred variant of the invention listed in table 1a (I1, I2, I3, I4, I5, I6 and I7) all show a high etch rate selectivity for etching of AlO$_x$ vs Cu layers (see results in table 2). Occurrence of "over-etching" (i.e. values of >100% etching) of the AlO$_x$-layer first disappears (in the time period applied) in compositions with pH value of 6.4 (or higher; see compositions I6 and I7). Compositions which have a pH of 6.4 (or higher, up to a pH of 7.5) are therefore regarded as preferred test compositions according to the invention.

Over-etching results demonstrate that deviations from optimal pH or composition can lead to an unfavourable increase in etch rates and hence in a loss of etch rate selectivity. A mere reduction of etch times in order to optimize etch results is not preferred as this can lead to more inaccuracy in etch time due to practical limitations. For example, the etch time of 1 min as selected for etching the AlO$_x$-layers in the present examples is an industrially relevant time period. For practical reasons, the etch rate achieved with a certain composition is relevant, not only the total etch loss.

In the pH range most preferred in practice (pH 6.8 to 7.5), compositions according to the first preferred variant of the invention which comprise an organic solvent have a stronger tendency to show incomplete etching results, with a sharp decline between pH values 7.1 and 7.3 (see compositions I4 and I5). In contrast, composition I1 which does not comprise organic solvents shows a high but controlled etch rate for the Cu layer (but no over-etching) in the preferred pH range, and a high etch rate selectivity. Compositions according to the first preferred variant of the invention which do not comprise organic solvents (see e.g. compositions I1 and I2) are therefore preferred.

Test compositions according to the first preferred variant of the invention listed in table 1b show a good (see compositions I19, I110 containing no organic solvent or a preferred organic solvent) or satisfactory (see compositions I11, I12 and I13, all containing butyl diglycol as a less preferred organic solvent) etch rate selectivity for etching of AlO$_x$ vs Cu layers. All test compositions listed in table 1b showed over-etching under the reaction conditions applied.

Comparative compositions listed in table 1c (C1, C2) did not show a satisfactory etch rate selectivity for etching of AlO$_x$ vs Cu layers, i.e. significant unfavourable etching of the Cu layer was observed in each case (see table 2 above).

Example 3: Preparation of Compositions According to the Invention (Second Preferred Variant) and of Comparative Compositions (not According to the Invention)

The following compositions according to the second preferred variant of the invention (compositions I20, I21 and I22) were prepared by mixing the components (A) to (D) and (G). Details are given below in table 3. In addition, comparative compositions (not according to the invention, compositions C20 and C21) were also prepared in a similar manner, as shown in more detail in table 4 below.

TABLE 3

Test compositions according to the invention (second preferred variant)

| Component | Constituent | Composition [wt.-%] | | |
|---|---|---|---|---|
| | | I20 | I21 | I22 |
| (A) | NFM | 10.0 | 5.0 | 5.0 |
| (B) | NH$_4$F | 0.03 | 0.03 | 0.03 |
| (C) | 5-Me-BTA | 0.75 | 0.5 | 0.8 |
| (C) | 5-Cl-BTA | 0.15 | 0 | 0 |
| (C) | BTA | 0 | 0.5 | 0.8 |
| (C) | Succinic acid | 0.12 | 0.1 | 0.1 |
| (D) | L-histidine | 0.1 | 0.1 | 0.1 |
| (G) | Water | 88.85 | 93.77 | 93.17 |
| — | pH: | 4.7 | 4.7 | 4.7 |

TABLE 4

Comparative test compositions

| Component | Constituent | Composition [wt.-%] | |
|---|---|---|---|
| | | C20 | C21 |
| (A) | NFM | 0 | 0 |
| (B) | NH$_4$F | 0.03 | 0.03 |
| (C) | 5-Me-BTA | 0.5 | 0.5 |
| (C) | 5-Cl-BTA | 0.1 | 0 |
| (C) | BTA | 0 | 0.5 |
| (C) | Succinic acid | 0.09 | 0.09 |
| (D) | L-histidine | 0.1 | 0.1 |
| (G) | Water | 99.28 | 98.88 |
| (H) | DMSO | 5.0 | 5.0 |
| — | pH: | 4.7 | 4.7 |

DMSO: dimethyl sulfoxide
All wt.-% of constituents in tables 3 and 4 are calculated as pure, undiluted compounds.

Example 4: Determination of Aluminium Oxide (AlOx) and Cobalt Etch Results of Test Compositions (Second Preferred Variant)

Si wafers or wafer pieces (collectively referred to as "test wafers" in the following) with the appropriate types of outer layers (Co; AlO$_x$; plasma-deposited tetraethyl orthosilicate ("TEOS")) were obtained from commercial sources. The test wafers were pre-treated as applicable: Co was immersed into an oxalic acid solution for 20-30 s and then rinsed with water and dried. AlO$_x$-coated surfaces were not pre-treated.

Aluminium oxide (AlO$_x$)-coated surfaces were used as a representative model for layers of (comprising or consisting of) an aluminium compound (as defined above).

The test compositions (as defined in tables 3 and 4) were prepared and the test wafers (see above) were contacted with the test compositions in a glass beaker, at a temperature of 40° C. and for a reaction time period of 1 min in the case of cobalt-coated surfaces, at a temperature of 35° C. and for a reaction time period of 15 s in the case of aluminium oxide-coated surfaces and at a temperature of 35° C. and for a reaction time period of 10 min in the case of TEOS surfaces. The test wafers were then withdrawn from the test compositions, rinsed with water or isopropanol and dried with nitrogen gas.

The thicknesses of the cobalt, TEOS and aluminium oxide layers on the test wafers were determined before and after contact with the test compositions by X-ray fluorescence analysis. Experiments were repeated at least three times to ensure reproducibility.

The difference of the measured value of the thickness of a cobalt, TEOS or AlOx layer, respectively, before its contact with a test composition, minus the measured value of the thickness of the same cobalt, TEOS or AlOx layer, respectively, after its contact with the test composition was determined in each case as the total etch loss and the total etch loss so determined was divided by the process time to yield the etch rate. The results are shown in table 5 below as etch rate of a layer after contact with a test composition in Å/min (each given value in table 5 representing the average of at least three experiments).

TABLE 5

Cobalt, TEOS and aluminium oxide etch results of the test compositions (second preferred variant)

| Composition | Etch rates per layer [Å/min] | | |
| --- | --- | --- | --- |
| | Co | AlO$_x$ | TEOS |
| I20 | 2.6 | 6.0 | <1 |
| I21 | 6.1 | no data | no data |
| I22 | 2.5 | no data | no data |
| C20 | 2.0 | 6.0 | <1 |
| C21 | 5.4 | no data | no data |

From the test results shown in table 5, the following observations can be made:

Composition I20 according to the invention shows a satisfactory etch rate selectivity for etching of AlO$_x$ vs Co and TEOS layers.

Compositions I22 according to the invention and C20 (comparative composition not according to the invention) show similar satisfactory results regarding etch rate selectivity for etching of AlO$_x$ vs Co layers (but see results of example 5, below).

Example 5: Stability of Test Compositions (Second Preferred Variant) Against Precipitation The test composition I20 according to the invention and the comparative test composition C20 were cooled to 5° C. for 72 h. Immediately after the cooling period, both compositions were visually inspected for stability of the solution (i.e. precipitated material).

It was found that composition I20 according to the invention had remained clear after the cooling period, indicating stability of the solution even at lowered temperatures, while comparative composition C20 showed precipitation of materials, indicating insufficient stability of the solution at temperatures below room temperature.

From these observations it can be concluded that compositions comprising a solubilizer according to the present invention (in composition I20: N-formylmorpholine) show enhanced stability of solution against precipitation in comparison with compositions comprising no or other solubilizers than the ones according to the present invention (in comparative composition C20: DMSO).

As is known in the field, compositions for etching one or more materials for use in the manufacture of a semiconductor device must remain stable under the conditions of manufacture and not, e.g., form precipitates which can interfere with or corrupt said manufacture process or its products. Therefore, compositions for etching one or more materials for use in the manufacture of a semiconductor device which form precipitates under the conditions of such manufacture process are not acceptable for industrial use.

What is claimed is:
1. A method comprising:
contacting a composition with a substrate,
wherein the composition comprises:
(A) at least one solubilizer, selected from the group consisting of
a compound of formula I:

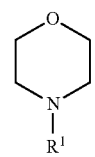

wherein $R^1$ is at least one selected from the group consisting of hydrogen and —C(O)—$R^2$ wherein $R^2$ is selected from the group consisting of hydrogen and alkyl having 1, 2, 3 or 4 carbon atoms;
a compound of formula II:

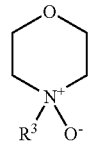

wherein $R^3$ is alkyl having 1, 2, 3 or 4 carbon atoms;
trimethylamine-N-oxide,
triethylamine-N-oxide,
triethanolamine-N-oxide,
pyridine-N-oxide,
N-ethylpyrrolidine-N-oxide, and
mixtures thereof;
(B) an etchant comprising fluoride anions;
(C) at least one corrosion inhibitor, selected from the group consisting of benzotriazole which is unsubstituted or substituted once or twice independently by $C_{1-4}$-alkyl, amino-$C_{1-4}$-alkyl, phenyl, thiophenyl, halogen, hydroxy, nitro and/or thiol;
ethylene urea, ethylene thiourea, 1,2,4-triazole, 5-aminotetrazole, 5-amino-1,3,4-thiadiazol-2-thiol, 3-amino-1H-1,2,4 triazole, 3,5-diamino-1,2,4-triazole, tolyltriazole, 3-amino-5-mercapto-1,2,4-triazole, 1-amino-1,2,4-triazole, 1-amino-1,2,3-triazole, 1-amino-5-methyl-1,2,3-triazole, 3-mercapto-1,2,4-triazole, 3-isopropyl-1,2,4-triazole, naphthotriazole, 1H-tetrazole-5-acetic acid, 1-phenyl-2-tetrazoline-5-thione, 4-methyl-2-phenylimidazole, 2-mercaptothiazoline, 2,4-diamino-6-methyl-1,3,5-triazine, thiazole, imidazole, benzimidazole, triazine, methyltetrazole, 1,3-dimethyl-2-imidazolidinone, 1,5-pentamethylenetetrazole, 1-phenyl-5-mercaptotetrazole, 2H-imidazole-2-thione, 4-methyl-4H-1,2,4-triazole-3-thiol, 5-amino-1,3,4-thiadiazole-2-thiol, benzothiazole, tritolyl phosphate, indazole, adenine, cytosine, guanine, thymine, 2,2'-azanediyldiacetic acid, propanethiol, citric acid, ascorbic acid, thiourea, 1,1,3,3-tetramethylurea, urea, uric acid, glycine, dodecylphosphonic acid, oxalic acid, malonic acid, succinic acid, nitrilotriacetic acid, and mixtures thereof;

(D) at least one chelating agent selected from the group consisting of histidine, 1,2-cyclohexylenedinitrilotetraacetic acid, 1,1,1,5,5,5-hexafluoro-2,4-pentanedione, acetylacetonate, 2,2'-azanediyldiacetic acid, ethylenediaminetetraacetic acid, etidronic acid, methanesulfonic acid, acetylacetone, 1,1,1-trifluoro-2,4-pentanedione, 1,4-benzoquinone, 8-hydroxyquinoline, salicylidene aniline; tetrachloro-1,4-benzoquinone, 2-(2-hydroxyphenyl)-benzoxazol, 2-(2-hydroxyphenyl)-benzothiazole, hydroxyquinoline sulfonic acid, sulfosalicylic acid, salicylic acid, pyridine, 2-ethylpyridine, 2-methoxypyridine, 3-methoxypyridine, 2-picoline, dimethylpyridine, piperidine, piperazine, triethylamine, triethanolamine, ethylamine, methylamine, isobutylamine, tert-butylamine, tributylamine, dipropylamine, dimethylamine, diglycol amine, monoethanolamine, methyldiethanolamine, pyrrole, isoxazole, bipyridine, pyrimidine, pyrazine, pyridazine, quinoline, isoquinoline, indole, 1-methylimidazole, diisopropylamine, diisobutylamine, aniline, pentamethyldiethylenetriamine, acetoacetamide, ammonium carbamate, ammonium pyrrolidinedithiocarbamate, dimethyl malonate, methyl acetoacetate, N-methyl acetoacetamide, tetramethylammonium thiobenzoate, 2,2,6,6-tetramethyl-3,5-heptanedione, tetramethylthiuram disulfide, lactic acid, ammonium lactate, formic acid, propionic acid, gamma-butyrolactone, and mixtures thereof; and (G) water, wherein the method is suitable for selectively etching a layer comprising an aluminum compound in the presence of a layer of a low-k material and/or a layer comprising copper and/or cobalt;

for selectively removing from a substrate a layer comprising an aluminum compound in the presence of a layer of a low-k material and/or a layer comprising copper and/or cobalt, and/or for selectively removing from a surface of a semiconductor substrate a layer comprising an aluminum compound in the presence of a layer of a low-k material and/or a layer comprising copper and/or cobalt.

2. The method according to claim 1, wherein the method comprises a two-step-process of removing (i) a metal hard mask, and (ii) an etch-stop layer of an aluminum compound deposited on a layer comprising copper and/or a layer comprising cobalt.

3. The method according to claim 1, wherein the at least one solubilizer (A) is selected from the group consisting of a compound of formula I; and a compound of formula II;

the etchant (B) is at least one selected from the group consisting of ammonium fluoride, ammonium bifluoride, triethanolammonium fluoride, diglycolammonium fluoride, methyldiethanolammonium fluoride, tetramethylammonium fluoride, triethylamine trihydrofluoride, hydrogen fluoride, fluoroboric acid, tetrafluoroboric acid, ammonium tetrafluoroborate, fluoroacetic acid, ammonium fluoroacetate, trifluoroacetic acid, fluorosilicic acid, ammonium fluorosilicate, tetrabutylammonium tetrafluoroborate, and mixtures thereof, and/or the at least one corrosion inhibitor (C) is selected from the group consisting of benzotriazole which is unsubstituted or substituted once or twice independently by $C_{1-4}$-alkyl, amino-$C_{1-4}$-alkyl, phenyl, thiophenyl, halogen, hydroxy, nitro and/or thiol;

succinic acid; and mixtures thereof.

4. The method according to claim 1, wherein the at least one chelating agent (D) is selected from the group consisting of histidine, 1,2-cyclohexylenedinitrilotetraacetic acid, and mixtures thereof, and/or the composition comprises as further component:

(E) a surfactant.

5. The method according to claim 1, wherein a pH of the composition is in the range of from 3.5 to 8, and/or the composition comprises as further component:

(F) a buffering system which is suitable to buffer a pH of the composition in the range of from 3.5 to 8.

6. The method according to claim 1, comprising (A) at least one solubilizer selected from the group consisting of a compound of formula I, and a compound of formula II;

(B) at least one etchant, selected from the group consisting of ammonium fluoride, ammonium bifluoride, triethanolammonium fluoride, diglycolammonium fluoride, methyldiethanolammonium fluoride, tetramethylammonium fluoride, triethylamine trihydrofluoride, hydrogen fluoride, fluoroboric acid, tetrafluoroboric acid, ammonium tetrafluoroborate, fluoroacetic acid, ammonium fluoroacetate, trifluoroacetic acid, fluorosilicic acid, ammonium fluorosilicate, tetrabutylammonium tetrafluoroborate, and mixtures thereof;

(C) at least one corrosion inhibitor, selected from the group consisting of benzotriazole which is unsubstituted or substituted once or twice independently by $C_{1-4}$-alkyl, amino-$C_{1-4}$-alkyl, phenyl, thiophenyl, halogen, hydroxy, nitro and/or thiol, succinic acid, and mixtures thereof, (D) at least one chelating agent selected from the group consisting of histidine, 1,2-cyclohexylenedinitrilotetraacetic acid, and mixtures thereof, and (G) water, wherein a pH of the composition is in the range of from 3.5 to 8.

7. The method according to claim 1, the composition comprising:

(A) at least one solubilizer, selected from the group consisting of 4-methylmorpholine-4-oxide, trimethylamine-N-oxide, triethylamine-N-oxide, triethanolamine-N-oxide, pyridine-N-oxide, N-ethylmorpholine-N-oxide, N-ethylpyrrolidine-N-oxide, and mixtures thereof;

(B) an etchant comprising fluoride anions;
(C) at least one corrosion inhibitor, selected from the group consisting of benzotriazole, 6-methyl-benzotriazole, 5-methyl-benzotriazole, ethylene urea, ethylene thiourea, 1,2,4-triazole, 5-aminotetrazole, 1-hydroxybenzotriazole, 5-amino-1,3,4-thiadiazol-2-thiol, 3-amino-1H-1,2,4 triazole, 3,5-diamino-1,2,4-triazole, tolyltriazole, 5-phenyl-benzotriazole, 5-nitro-benzotriazole, 3-amino-5-mercapto-1,2,4-triazole, 1-amino-1,2,4-triazole, 2-(5-amino-pentyl)-benzotriazole, 1-amino-1,2,3-triazole, 1-amino-5-methyl-1,2,3-triazole, 3-mercapto-1,2,4-triazole, 3-isopropyl-1,2,4-triazole, 5-phenylthiol-benzotriazole, halobenzotriazoles, naphthotriazole, 1H-tetrazole-5-acetic acid, 2-mercaptobenzothiazole, 1-phenyl-2-tetrazoline-5-thione, 2-mercaptobenzimidazole, 4-methyl-2-phenylimidazole, 2-mercaptothiazoline, 2,4-diamino-6-methyl-1,3,5-triazine, thiazole, imidazole, benzimidazole, triazine, methyltetrazole, 1,3-dimethyl-2-imidazolidinone, 1,5-pentamethylenetetrazole, 1-phenyl-5-mercaptotetrazole, 2H-imidazole-2-thione, 4-methyl-4H-1,2,4-triazole-3-thiol, 5-amino-1,3,4-thiadiazole-2-thiol, benzothiazole, tritolyl phosphate, indazole, adenine, cytosine, guanine, thymine, 2,2'-azanediyldiacetic acid, propanethiol, citric acid, ascorbic acid, thiourea, 1,1,3,3-tetramethylurea, urea, uric acid, glycine, dodecylphosphonic acid, oxalic acid, malonic acid, succinic acid, nitrilotriacetic acid, and mixtures thereof;
(D) at least one chelating agent selected from the group consisting of 1,2-cyclohexylenedinitrilotetraacetic acid, 1,1,1,5,5,5-hexafluoro-2,4-pentane-dione, acetylacetonate, 2,2'-azanediyldiacetic acid, ethylenediaminetetraacetic acid, etidronic acid, methanesulfonic acid, acetylacetone, 1,1,1-trifluoro-2,4-pentanedione, 1,4-benzoquinone, 8-hydroxyquinoline, salicylidene aniline; tetrachloro-1,4-benzoquinone, 2-(2-hydroxyphenyl)-benzoxazol, 2-(2-hydroxyphenyl)-benzothiazole, hydroxyquinoline sulfonic acid, sulfosalicylic acid, salicylic acid, pyridine, 2-ethylpyridine, 2-methoxypyridine, 3-methoxypyridine, 2-picoline, dimethylpyridine, piperidine, piperazine, triethylamine, triethanolamine, ethylamine, methylamine, isobutylamine, tert-butylamine, tributylamine, dipropylamine, dimethylamine, diglycol amine, monoethanolamine, methyldiethanolamine, pyrrole, isoxazole, bipyridine, pyrimidine, pyrazine, pyridazine, quinoline, isoquinoline, indole, 1-methylimidazole, diisopropylamine, diisobutylamine, aniline, pentamethyldiethylenetriamine, acetoacetamide, ammonium carbamate, ammonium pyrrolidinedithiocarbamate, dimethyl malonate, methyl acetoacetate, N-methyl acetoacetamide, tetramethylammonium thiobenzoate, 2,2,6,6-tetramethyl-3,5-heptanedione, tetramethylthiuram disulfide, lactic acid, ammonium lactate, formic acid, propionic acid, gamma-butyrolactone, and mixtures thereof;
(E) at least one surfactant;
(F) a buffering system which is suitable to buffer a pH of the composition in the range of from 6 to 8, and
(G) water,
wherein the pH of the composition is in the range of from 6 to 8.

8. The method according to claim 1, wherein the total amount of the at least one solubilizer (A) present is in the range of from 0.01 to 20 wt. % based on the total weight of the composition.

9. The method according to claim 1, wherein the total amount of the at least one etchant (B) present is in the range of from 0.001 to 1 wt. % based on the total weight of the composition.

10. The method according to claim 1, wherein the total amount of the at least one corrosion inhibitor (C) present is in the range of from 0.01 to 4 wt.-% based on the total weight of the composition.

11. The method according to claim 1, wherein the component (B) is ammonium fluoride.

12. The method according to claim 1, wherein the chelating agent (D) is L-histidine.

13. The method according to claim 1, wherein the at least one corrosion inhibitor (C) is benzotriazole which is unsubstituted or substituted once or twice independently by $C_{1-4}$ alkyl and/or halogen.

14. The method according to claim 1, wherein the total amount of the at least one solubilizer (A) present is in the range of from 2 to 15 wt. %, based on the total weight of the composition.

15. A process for manufacturing a semiconductor device, the process comprising:
selectively etching a surface of a semiconductor substrate comprising at least one layer comprising or consisting of an aluminum compound in the presence of a layer of a low-k material and/or a layer comprising copper and/or cobalt, by contacting the at least one layer of an aluminum compound at least once with a composition comprising:
(A) at least one solubilizer, selected from the group consisting of
a compound of formula I:

(I)

wherein $R^1$ is at least one selected from the group consisting of hydrogen and —C(O)—$R^2$ wherein $R^2$ is selected from the group consisting of hydrogen and alkyl having 1, 2, 3 or 4 carbon atoms;
a compound of formula II:

(II)

wherein $R^3$ is alkyl having 1, 2, 3 or 4 carbon atoms;
trimethylamine-N-oxide,
triethylamine-N-oxide,
triethanolamine-N-oxide,
pyridine-N-oxide,
N-ethylpyrrolidine-N-oxide, and
mixtures thereof;
(B) an etchant comprising fluoride anions;
(C) at least one corrosion inhibitor, selected from the group consisting of benzotriazole which is unsubstituted or substituted once or twice independently by $C_{1-4}$-alkyl, amino-$C_{1-4}$-alkyl, phenyl, thiophenyl, halogen, hydroxy, nitro and/or thiol;

ethylene urea, ethylene thiourea, 1,2,4-triazole, 5-aminotetrazole, 5-amino-1,3,4-thiadiazol-2-thiol, 3-amino-1H-1,2,4 triazole, 3,5-diamino-1,2,4-triazole, tolyltriazole, 3-amino-5-mercapto-1,2,4-triazole, 1-amino-1,2,4-triazole, 1-amino-1,2,3-triazole, 1-amino-5-methyl-1,2,3-triazole, 3-mercapto-1,2,4-triazole, 3-isopropyl-1,2,4-triazole, naphthotriazole, 1H-tetrazole-5-acetic acid, 1-phenyl-2-tetrazoline-5-thione, 4-methyl-2-phenylimidazole, 2-mercaptothiazoline, 2,4-diamino-6-methyl-1,3,5-triazine, thiazole, imidazole, benzimidazole, triazine, methyltetrazole, 1,3-dimethyl-2-imidazolidinone, 1,5-pentamethylenetetrazole, 1-phenyl-5-mercaptotetrazole, 2H-imidazole-2-thione, 4-methyl-4H-1,2,4-triazole-3-thiol, 5-amino-1,3,4-thiadiazole-2-thiol, benzothiazole, tritolyl phosphate, indazole, adenine, cytosine, guanine, thymine, 2,2'-azanediyldiacetic acid, propanethiol, citric acid, ascorbic acid, thiourea, 1,1,3,3-tetramethylurea, urea, uric acid, glycine, dodecylphosphonic acid, oxalic acid, malonic acid, succinic acid, nitrilotriacetic acid, and mixtures thereof;

(D) at least one chelating agent selected from the group consisting of histidine, 1,2-cyclohexylenedinitrilotetraacetic acid, 1,1,1,5,5,5-hexafluoro-2,4-pentanedione, acetylacetonate, 2,2'-azanediyldiacetic acid, ethylenediaminetetraacetic acid, etidronic acid, methanesulfonic acid, acetylacetone, 1,1,1-trifluoro-2,4-pentanedione, 1,4-benzoquinone, 8-hydroxyquinoline, salicylidene aniline; tetrachloro-1,4-benzoquinone, 2-(2-hydroxyphenyl)-benzoxazol, 2-(2-hydroxyphenyl)-benzothiazole, hydroxyquinoline sulfonic acid, sulfosalicylic acid, salicylic acid, pyridine, 2-ethylpyridine, 2-methoxypyridine, 3-methoxypyridine, 2-picoline, dimethylpyridine, piperidine, piperazine, triethylamine, triethanolamine, ethylamine, methylamine, isobutylamine, tert-butylamine, tributylamine, dipropylamine, dimethylamine, diglycol amine, monoethanolamine, methyldiethanolamine, pyrrole, isoxazole, bipyridine, pyrimidine, pyrazine, pyridazine, quinoline, isoquinoline, indole, 1-methylimidazole, diisopropylamine, diisobutylamine, aniline, pentamethyldiethylenetriamine, acetoacetamide, ammonium carbamate, ammonium pyrrolidinedithiocarbamate, dimethyl malonate, methyl acetoacetate, N-methyl acetoacetamide, tetramethylammonium thiobenzoate, 2,2,6,6-tetramethyl-3,5-heptanedione, tetramethylthiuram disulfide, lactic acid, ammonium lactate, formic acid, propionic acid, gamma-butyrolactone, and mixtures thereof; and (G) water.

16. The process according to claim 15, wherein the at least one layer comprising or consisting of an aluminum compound is a top layer and the layer comprising copper and/or cobalt is a lower layer covered by the top layer, with or without at least one further layer being present in between the top layer and the lower layer.

17. The process according to claim 15, the process comprising a two-step cleaning process, the process comprising
   removing in a first step a metal hard mask,
   before selectively etching in a separate second step the at least one layer comprising or consisting of an aluminum compound.

18. The process according to claim 15, wherein the at least one layer comprising or consisting of an aluminum compound before etching has a maximum thickness of 30 nm or below.

19. The process according to claim 15, wherein the selectively etching is conducted in the presence of a layer of a low k material and a layer comprising copper and/or cobalt.

* * * * *